US011725222B2

(12) United States Patent
Griswold, Jr. et al.

(10) Patent No.: US 11,725,222 B2
(45) **Date of Patent: *Aug. 15, 2023**

(54) CLEAVABLE NUCLEOTIDE ANALOGS AND USES THEREOF

(71) Applicant: President and Fellows of Harvard College, Cambridge, MA (US)

(72) Inventors: Kettner John Frederick Griswold, Jr., Brookline, MA (US); Richard E. Kohman, Cambridge, MA (US); George M. Church, Brookline, MA (US); Jonathan Rittichier, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 941 days.

This patent is subject to a terminal disclaimer.

(21) Appl. No.: 16/465,733

(22) PCT Filed: Nov. 30, 2017

(86) PCT No.: PCT/US2017/063961

§ 371 (c)(1),
(2) Date: May 31, 2019

(87) PCT Pub. No.: WO2018/102554

PCT Pub. Date: Jun. 7, 2018

(65) Prior Publication Data

US 2020/0080122 A1 Mar. 12, 2020

Related U.S. Application Data

(60) Provisional application No. 62/428,842, filed on Dec. 1, 2016.

(51) Int. Cl.

| | |
|---|---|
| ***C12P 19/34*** | (2006.01) |
| ***C07H 19/10*** | (2006.01) |
| ***C07H 19/20*** | (2006.01) |
| ***C07H 21/02*** | (2006.01) |
| ***C07H 21/04*** | (2006.01) |

(52) U.S. Cl.

CPC .............. *C12P 19/34* (2013.01); *C07H 19/10* (2013.01); *C07H 19/20* (2013.01); *C07H 21/02* (2013.01); *C07H 21/04* (2013.01)

(58) Field of Classification Search

CPC ........ C07H 19/10; C07H 19/20; C07H 21/02; C07H 21/04; C12P 19/34

See application file for complete search history.

(56) References Cited

U.S. PATENT DOCUMENTS

| | | | | |
|---|---|---|---|---|
| 5,990,300 | A | 11/1999 | Hiatt et al. | |
| 6,287,821 | B1 | 9/2001 | Shi et al. | |
| 10,774,366 | B2 * | 9/2020 | Church | C40B 40/06 |
| 2016/0265048 | A1 | 9/2016 | Ju et al. | |
| 2019/0062804 | A1 * | 2/2019 | Church | C12Q 1/6806 |

FOREIGN PATENT DOCUMENTS

| | | | | |
|---|---|---|---|---|
| WO | 2009/051807 | A1 | 4/2009 | |
| WO | WO-2017176541 | A1 * | 10/2017 | C12P 19/34 |
| WO | WO-2017196783 | A1 * | 11/2017 | C12P 19/34 |

OTHER PUBLICATIONS

Turcatti et al. (Nucleic Acids Research, 2008, vol. 36, No. 4 e25 pp. 1-13). (Year: 2008).*

Prykota et al. "Nucleotides Part LXXX: Synthesis of 3'-O Fluorescence Labeled Thymidine Derivatives and Their 5'-O-Triphosphates" Nucleosides, Nucleotides & Nucleic Acids (2011), 30(7-8), 544-551. (Year: 2011).*

Palla, M. et al. 'DNA sequencing by synthesis using 3'-0-azidomethyl nucleotide reversible terminators and surface-enhanced Raman spectroscopic detection'; Jan. 1, 2014, RSC Advances; vol. 4, Issue 90, pp. 1-11; p. 9, figure 1.

* cited by examiner

*Primary Examiner* — Jezia Riley

(74) *Attorney, Agent, or Firm* — Banner & Witcoff, Ltd.

(57) ABSTRACT

Cleavable nucleotide analogs are provided. The nucleotide analog includes a nucleotide molecule attached to a cleavable moiety wherein the cleavable moiety comprises a protective group and/or a linker attached to a fluorophore. The cleavable moiety is linked to the oxygen atom of the 3'-OH of the pentose of the nucleotide molecule. The nucleotide analogs can be used in making polynucleotide molecules using template independent polymerases. The nucleotide analogs can act as reversible terminators during DNA sequencing by synthesis. The cleavage of the cleavable moiety restores a free 3'-OH functional group allowing growth of the polynucleotide molecule. The general structures as well as proposed synthetic schemes for the nucleotide analogs are also provided.

14 Claims, 21 Drawing Sheets light
$H_2O$
light
$H_2O$
Dye
Dye
Dye
Dye
$CO_2$

X = A, T, C, or G
PPh3
Dye
OR
X = A, T, C, or G
PPh3
Dye
CO2

Pd(PPh$_3$)$_4$
X = A, T, C, or G
Dye
OR
Pd(PPh$_3$)$_4$
X = A, T, C, or G
$CO_2$
Dye $CH_2Cl_2$
PPTS, MeOH
1) $(Bu_3NH)_4F$
2) $POCl_3$ / $PO(OMe)_3$
3) $(Bu_3NH)_4P_2O_7$
4) $Bu_3N$ / TEAB
5) $NH_3$ (aq)

TBSO
OH
NH
1.CDI, THF
HO
KOH (cat)
2. TBAF, THF
HO
3. POCl3/ PO(OMe)3
4. (Bu3NH)4P2O7
5. Bu3N/TEAB
ACdNTP 3. $POCl_3$/ $PO(OMe)_3$
4. $(Bu_3NH)_4P_2O_7$
5. $Bu_3N$/TEAB 1.NaH
Br
2. TBAF, THF

CLEAVABLE NUCLEOTIDE ANALOGS AND USES THEREOF

RELATED APPLICATIONS

This application is a National Stage Application under 35 U.S.C. 371 of co-pending PCT application PCT/US17/63961 designating the United States and filed Nov. 30, 2017; which claims the benefit of U.S. provisional application No. 62/428,842 filed on Dec. 1, 2016 each of which are hereby incorporated by reference in their entireties.

STATEMENT OF GOVERNMENT INTERESTS

This invention was made with government support under grant numbers RM1HG008525 and R01MH103910 awarded by National Institutes of Health. The government has certain rights in the invention.

FIELD

The present invention relates in general to methods of making polynucleotides with cleavable nucleotide analogs.

BACKGROUND

With the rapid development of new generations of sequencing technology, reversible terminators have been developed as substrates for DNA polymerases in DNA sequencing methods such as DNA sequencing by synthesis. Reversible termination sequencing is one of the sequencing by synthesis strategies that uses modified nucleotide analogs to terminate primer extension reversibly. There are in general two types of reversible terminators based on the different reversible blocking groups. The first type is 3'-O-blocked reversible terminators where the reversible terminating group is linked to the oxygen atom of the 3'-OH of the pentose and the fluorescent moiety being cleavably linked to the base of the nucleotide molecule. The cleavable fluorescent moiety acts as a reporter. The second type is 3'-unblocked reversible terminators where the reversible terminating group and the fluorescent moiety are linked to the base of the nucleotide molecule. The fluorescent moiety functions as a reporter and as part of the reversible terminating group for termination of the primer extension (See, e.g., Fei Chen, et al., The History and Advances of Reversible Terminators Used in New Generations of Sequencing Technology, Genomics Proteomics Bioinformatics, 2013, Vol. 11, pages 34-40, hereby incorporated by reference in its entirety). There is a continuing need in the art to improve and facilitate DNA synthesis with other nucleotide analogs.

SUMMARY

According to one aspect, the present disclosure provides cleavable nucleotide analogs including a nucleotide molecule attached to a cleavable moiety wherein the cleavable moiety comprises a protective group, a linker or a linker lengthening moiety. In some embodiments, protective group, the linker or the linker lengthening moiety may be attached to a detectable moiety, including but not limited to a fluorescent moiety or a fluorophore. The cleavable moiety is linked to the oxygen atom of the 3'-OH of the pentose of the nucleotide molecule.

According to another aspect, the present disclosure provides methods of making polynucleotides using the cleavable nucleotide analogs. In certain embodiments, template independent polymerases are used in the methods of making polynucleotides. In other embodiments, the cleavable nucleotide analogs act as reversible terminators during DNA sequencing by synthesis. In further embodiments, the cleavage of the cleavable moiety restores a free 3'-OH functional group allowing growth of the polynucleotide molecule.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DETAILED DESCRIPTION

Figure 1:
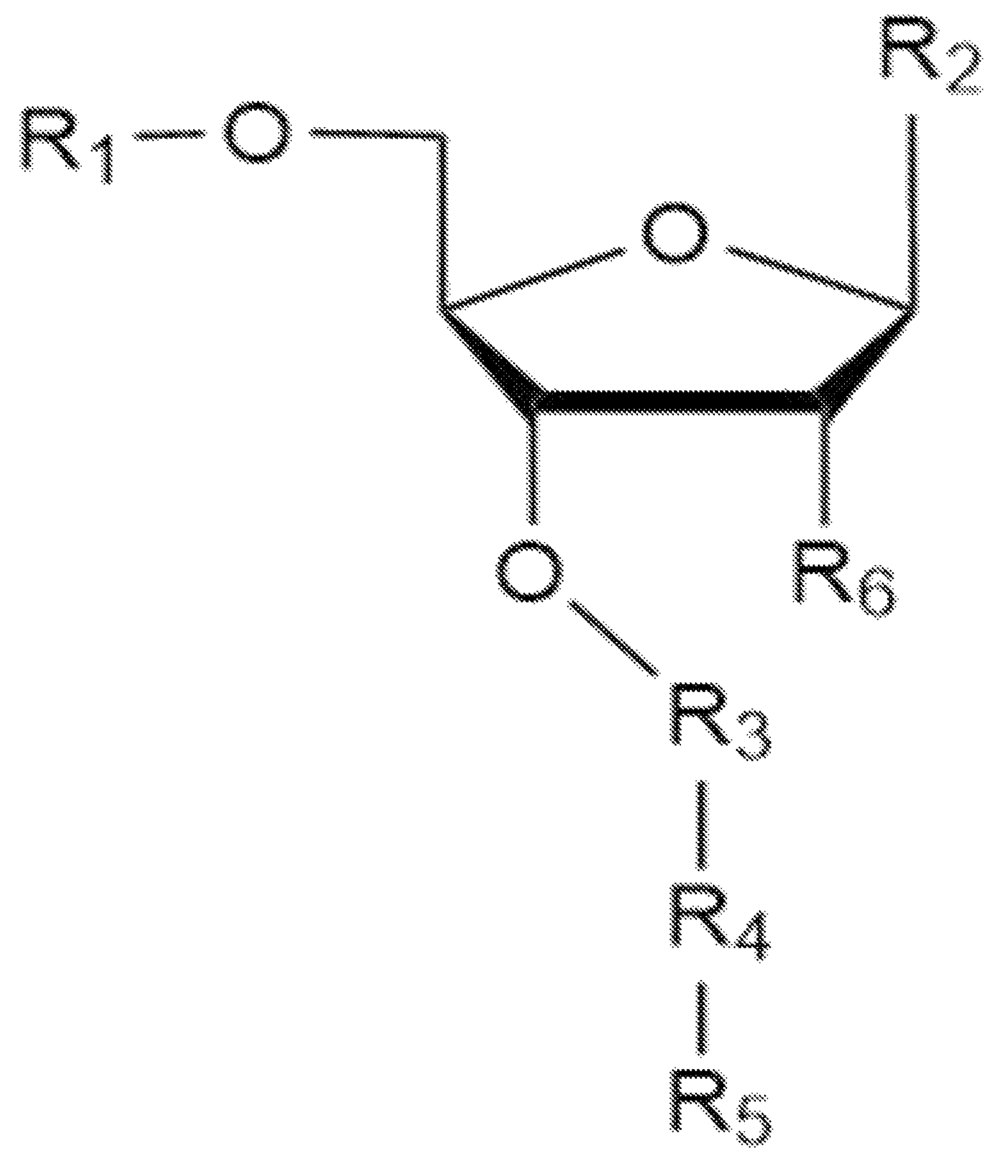
FIG. 1 depicts a general structure of a nucleotide analog represented by formula I.

Embodiments of the present disclosure provides cleavable nucleotide analogs having the structure represented by formula I:

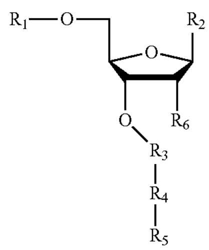

In formula I, $R_1$ is H, a monophosphate, a diphosphate, a triphosphate or a nucleic acid $R_2$ is a nucleobase or a modified nucleobase, $R_3$ is a cleavable moiety, $R_4$ is absent or a linker lengthening moiety, $R_5$ is absent or a detectable moiety, and $R_6$ is H or OH.

Embodiments of the present disclosure also provide pharmaceutically acceptable salts, solvates or hydrates and prodrugs prepared from the cleavable nucleotide analogs of formula I.

In exemplary embodiments, the cleavable moiety includes a protective group, a linker or a linker lengthening moiety. In some embodiments, the protective group, the linker or the linker lengthening moiety may be attached to a detectable moiety, including but not limited to a fluorescent moiety or a fluorophore. In certain embodiments, the protective group and/or the linker is attached to the fluorophore via chemical conjugation. In some embodiments, linker molecules are included to join the protective group and the fluorophore. In some embodiments, the nucleotide molecule is a deoxyribonucleotide or a ribonucleotide. In certain embodiments, the nucleotide molecule is a modified nucleotide. In some embodiments, the protective group is linked to the nucleobase or the pentose of the nucleotide molecule. In exemplary embodiments, the protective group is reversibly linked to the oxygen atom of the 3'-OH of the pentose of the nucleotide molecule. In some embodiments, the protective group comprises ethers, esters, carbonates, carbamates or silyl ethers, or their derivatives. In certain embodiments, the cleavable moiety is photocleavable, thermo-cleavable, electrochemically cleavable, transition metal cleavable or cleavable by a change in pH. The cleavable nucleotide analogs of the present disclosure are useful for making polynucleotides and as reversible terminators in DNA sequencing methods such as sequencing by synthesis.

Embodiments of the present disclosure further provide methods of making a polynucleotide. In certain embodiments, the method includes combining a selected nucleotide analog of claim 1, one or more cations, and a template-independent polymerase in an aqueous reaction medium including a target substrate comprising an initiator sequence and having a 3' terminal nucleotide attached to a single stranded portion, such that the template-independent polymerase interacts with the target substrate under conditions which covalently adds one of the selected nucleotide analog to the 3' terminal nucleotide. In further embodiments, the methods further include removing the cleavable moiety from the 3' terminal nucleotide analog of the extended target substrate and restoring a free 3'-OH group of the 3' terminal nucleotide. In other embodiments, the methods further include repeatedly introducing a subsequent selected nucleotide analog to the aqueous reaction medium under conditions which enzymatically add one of the subsequent selected nucleotide analog to the target substrate and removing the cleavable moiety from the 3' terminal nucleotide analog of the extended target substrate and restoring a free 3'-OH group of the 3' terminal nucleotide until the polynucleotide is formed. In one embodiment, the template-independent polymerase is a template-independent DNA or RNA polymerase. In another embodiment, the template-independent polymerase is a template-independent DNA polymerase. In exemplary embodiment, the template-independent polymerase is a terminal deoxynucleotidyl transferase (TdT).

Nucleic Acids and Nucleotides

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof.

An oligonucleotide is typically composed of a specific sequence of four nucleotide bases: adenine (A); cytosine (C); guanine (G); and thymine (T) (uracil (U) for thymine (T) when the polynucleotide is RNA). According to certain aspects, deoxynucleotide triphosphates (dNTPs, such as dATP, dCTP, dGTP, dTTP) may be used. According to certain aspects, ribonucleotide triphosphates (rNTPs, such as rATP, rCTP, rGTP, rUTP) may be used. According to certain aspects, ribonucleotide diphosphates (rNDPs) may be used.

The term "oligonucleotide sequence" or simply "sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. The present disclosure contemplates any deoxyribonucleotide or ribonucleotide and chemical variants thereof, such as methylated, hydroxymethylated or glycosylated forms of the bases, and the like. Natural nucleotides lack chain terminating moieties. According to another aspect, the methods of making the nucleic acids described herein use reversibly chain terminating nucleic acids, also known as reversible terminators to those of skill in the art.

As used herein the term nucleotide means a ribose or deoxyribose sugar having nucleobase attached at the 2' carbon. As used herein the term 'nucleobase' means a nucleotide base. Nucleobases are typically attached by a glycosidic bond to a pentose sugar ring, such as ribose, or deoxyribose at the 2' position. Exemplary nucleobases include adenine (A); cytosine (C); guanine (G); thymine (T); and uracil (U) or chemical variants thereof. The present disclosure contemplates any deoxyribonucleotide or ribonucleotide and chemical variants thereof, such as methylated, hydroxymethylated or glycosylated forms of the nucleobases, and their polyphosphate derivatives. In certain aspects, deoxynucleotide polyphosphates such derivatives of deoxynucleotide triphosphates, dNTPs, such as dATP, dCTP, dGTP, or dTTP, may be used.

Examples of modified nucleobases include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

Modified nucleotide mono, di, tri phosphates and their synthesis methods have been described (Roy, B., Depaix, A., Périgaud, C., & Peyrottes, S, (2016), Recent Trends in Nucleotide Synthesis. Chemical Reviews, 116(14), 7854-7897), which is hereby incorporated by reference in its entirety.

Polymerases

According to certain embodiments of the present disclosure, polymerases are used to make polynucleotides with selected cleavable nucleotide analogs. The polynucleotides contain information which is referred to herein as being recorded or stored in the polynucleotide sequence. Polymerases are enzymes that produce a polynucleotide or nucleic acid sequence, for example, using DNA or RNA as a template. Polymerases that produce RNA polymers are known as RNA polymerases, while polymerases that produce DNA polymers are known as DNA polymerases. Polymerases that incorporate errors are known in the art and are referred to herein as "error-prone polymerases". Template independent polymerases may be error prone polymerases. Using an error-prone polymerase allows the incorporation of specific bases at precise locations of the DNA molecule. Error-prone polymerases will either accept a non-standard base, such as a reversible chain terminating base, or will incorporate a different nucleotide, such as a nucleotide analog, a natural or unmodified nucleotide that is selectively provided during primer extension.

Template Independent Polymerases

As used herein, template-independent polymerases, refer to polymerase enzymes which catalyze extension of polynucleotide primer strand with nucleotides in the absence of a polynucleotide template. Template independent polymerases where the polynucleotide primer is DNA are known as template independent DNA polymerases. Template independent polymerases where the polynucleotide primer is RNA are known as template independent RNA polymerases. Template independent polymerases may accept a broad range of nucleotide polyphosphate substrates. Template independent DNA polymerase are defined to include all enzymes with activity classified by the Enzyme commission number EC 2.7.7.31 (See, enzyme—ExPASy: SIB Bioinformatics Resource Portal, EC 2.7.7.31).

According to certain aspects of the present disclosure, the template independent DNA polymerase is a terminal deoxynucleotidyl transferase (TdT) of the polX family of DNA polymerases. TdT may also be referred to as DNA nucleotidylexotransferase, (DNTT) or simply terminal transferase. According to further aspects of the disclosure, TdT is of mammalian origin, for example, from bovine or murine sources. Further description of TdT is provided in Biochim Biophys Acta., May 2010; 1804(5): 1151-1166, hereby incorporated by reference in its entirety. TdT creates polynucleotide strands by catalyzing the addition of nucleotides to the 3' terminus of a DNA molecule in the absence of a template. The preferred substrate of TdT is a 3'-overhang, but it can also add nucleotides to blunt or recessed 3' ends. Cobalt is a cofactor, however the enzyme catalyzes reaction upon Mg2+, Zn2+, and Mn+ administration in vitro. Nucleic acid initiator fragments or sequences may be 4 or 5 nucleotides or longer and may be single stranded or double stranded. Double stranded initiators may have a 3' overhang or they may be blunt ended or they may have a 3' recessed end. Preferred nucleotides are dTTP, dATP, dGTP, dCTP. TdT can catalyze incorporation of many modified nucleotides.

According to certain aspects of the disclosure, the template independent DNA polymerase is a terminal deoxynucleotidyl transferase of the archaeo-eukaryotic primase (AEP) superfamily. Exemplary terminal transferases are described in Guilliam, T. A., Keen, B. A., Brissett, N. C., & Doherty, A. J, (2015), Primase-polymerases are a functionally diverse superfamily of replication and repair enzymes, Nucleic Acids Research, 43(14), 6651-64, which is hereby incorporated by reference in its entirety.

In further aspects of the disclosure, the terminal transferase is PolpTN2, a DNA primase-polymerase protein encoded by the pTN2 plasmid from *Thermococcus nautilus*. In further aspects of the contemplated disclosure a C-terminal truncation of PolpTN2 may be used, such as $\Delta_{311-923}$. (see Sukhvinder Gill et al., A highly divergent archaeo-eukaryotic primase from the *Thermococcus nautilus* plasmid, pTN2, Nucleic Acids Research, Volume 42, Issue 6, Pp. 3707-3719, http://doi.org/10.1093/nar/gkt1385).

In further aspects of the disclosure, the terminal transferase is PriS, a primase S subunit from the kingdom Archea. For example: DNA primase complex of p41-p46 or PriSL as described in the following:

*Pyrococcus furiosus* (Lidong Liu et al., The Archaeal DNA Primase Biochemical Characterization of the p41-p46 Complex from *Pyrococcus Furiosus*, The Journal of Biological Chemistry, 276, 45484-45490, 2001, doi:10.1074/jbc.M106391200),

*Thermococcus kodakaraensis* (Wiebke Chemnitz Galal et al., Characterization of DNA Primase Complex Isolated from the Archaeon, *Thermococcus kodakaraensis*, The Journal of Biological Chemistry 287, 16209-16219, 2012, doi:10.1074/jbc.M111.338145),

*Sulfolobus solfataricus* (Si-houy Lao-Sirieix, et al., The Heterodimeric Primase of the Hyperthermophilic Archaeon *Sulfolobus solfataricus* Possesses DNA and RNA Primase, Polymerase and 3'-terminal Nucleotidyl Transferase Activities, Journal of Molecular Biology, Volume 344, Issue 5, 2004, Pages 1251-1263, http://dx.doi.org/10.1016/j.jmb.2004.10.018),

*Pyrococcus horikoshii* (Eriko Matsui et al., Distinct Domain Functions Regulating de Novo DNA Synthesis of Thermostable DNA Primase from Hyperthermophile *Pyro-*

*coccus horikoshii, Biochemistry,* 2003, 42 (50), pp 14968-14976, DOI: 10.1021/bi035556o), and

*Archaeoglobus fulgidus* (Stanislaw K. Jozwiakowski, et al., Archaeal replicative primases can perform translesion DNA synthesis, PNAS, 2015, vol. 112, no. 7, E633-E638, doi: 10.1073/pnas.1412982112), which are hereby incorporated by reference in their entireties.

In further aspects of the disclosure, the terminal transferase is an archeal non-homologous end joining archaeo-eukaryotic primase.

In further aspects of the disclosure, the terminal transferase is a mammalian Pol θ as described in Tatiana Kent, et al., Mechanism of microhomology-mediated end-joining promoted by human DNA polymerase θ, *Nature Structural &Molecular Biology*, Vol. 22, 230-237, (2015), doi:10.1038/nsmb.2961, hereby incorporated by reference in its entirety.

In further aspects of the disclosure, the terminal transferase is a Eukaryotic PrimPol, for example, human primPol have been described in Sara Garcia-Gomez, et al., PrimPol, an Archaic Primase/Polymerase Operating in Human Cells, Molecular Cell, Volume 52, Issue 4, 2013, Pages 541-553, http://dx.doi.org/10.1016/j.molcel.2013.09.025; Thomas A. Guilliam, et al., Human PrimPol is a highly error-prone polymerase regulated by single-stranded DNA binding proteins, Nucl. Acids Res., (2015), 43 (2): 1056-1068, doi: 10.1093/nar/gku1321, each of which is hereby incorporated by reference in its entirety.

Detectable Moieties

The present disclosure provides the following examples of detectable moieties, such as fluorescent moieties or fluorophores. Other detectable moieties such as radioactive labels or raman active labels can be used in the present invention. Exemplary radioactive labels include $^{2}H$, $^{3}H$, $^{11}C$, $^{13}C$, $^{14}C$, $^{13}N$, $^{32}P$, $^{15}O$, $^{33}S$, $^{34}S$, $^{35}S$, $^{36}S$. Exemplary Raman labels include Alkyne, Diyne, Nitriles, and the like. Raman methods of detection are described in Hiroyuki Yamakoshi, et al., Alkyne-Tag Raman Imaging for Visualization of Mobile Small Molecules in Live Cells, 2012, J. Am. Chem. Soc., 134 (51), pp 20681-20689, DOI: 10.1021/ja308529n, hereby incorporated by reference in its entirety.

According to certain embodiments, the fluorophores that can be attached to a cleavable protecting group (reversible terminating group) useful in the method described herein such as Methoxycoumarin, Dansyl, Pyrene, Alexa Fluor 350, AMCA, Marina Blue dye, Dapoxyl dye, Dialkylaminocoumarin, Bimane, Hydroxycoumarin, Cascade Blue dye, Pacific Orange dye, Alexa Fluor 405, Cascade Yellow dye, Pacific Blue dye, PyMPO, Alexa Fluor 430, NBD, QSY 35, Fluorescein, Alexa Fluor 488, Oregon Green 488, BODIPY 493/503, Rhodamine Green dye, BODIPY FL, 2',7'-Dichloro-, fluorescein, Oregon Green 514, Alexa Fluor 514, 4',5'-Dichloro-, 2',7'-dimethoxy-, fluorescein (JOE), Eosin, Rhodamine 6G, BODIPY R6G, Alexa Fluor 532, BODIPY 530/550, BODIPY TMR, Alexa Fluor 555, Tetramethyl-, rhodamine (TMR), Alexa Fluor 546, BODIPY 558/568, QSY 7, QSY 9, BODIPY 564/570, Lissamine rhodamine B, Rhodamine Red dye, BODIPY 576/589, Alexa Fluor 568, X-rhodamine, BODIPY 581/591, BODIPY TR, Alexa Fluor 594, Texas Red dye, Naphthofluorescein, Alexa Fluor 610, BODIPY 630/650, Malachite green, Alexa Fluor 633, Alexa Fluor 635, BODIPY 650/665, Alexa Fluor 647, QSY 21, Alexa Fluor 660, Alexa Fluor 680, Alexa Fluor 700, Alexa Fluor 750, and Alexa Fluor 790 and the like. It is to be understood that fluorophores are known to those of skill in the art and can be readily identified by literature search.

Exemplary fluorophores may be derivatized with amines, sulfhydryls, carboxylic acids, hydroxyls, succinimidyl esters, maleimides, and other reactive groups. Methods for attachment of derivatized fluorophores are known to those of skill in the art as conjugation. A review of the art of conjugation is hereby incorporated by reference in its entirety, see Hermanson, G. T., (2013), Bioconjugate Techniques, Academic Press.

Linkers

According to certain aspects of the present disclosure, linker portion of the cleavable moiety may be used. Linkers are result of coupling molecules containing complementary reactive moieties at their termini. Linkers may be accessed from the following exemplary precursors.

| Moieties for Attachment | Activated Precursors |
| --- | --- |
| Amine-to-amine | Di NHS esters/di isocyanates/di isothiocyanates/di acid halide/di anhydride. For example: Bis[2-(N-succinimidyl-oxycarbonyloxy)ethyl] sulfone, Di(N-succinimidyl) glutarate, Sebacic acid bis(N-succinimidyl) ester, p-Phenylene diisothiocyanate, 4,7,10,13,16,19,22,25,32,35,38,41,44,47,50,53-Hexadecaoxa-28,29-dithiahexapentacontanedioic acid di-N-succinimidyl ester, DTSSP (3,3'-dithiobis(sulfo-succinimidyl propionate)), Sulfo-EGS (ethylene glycol bis(sulfosuccinimidyl succinate)), DST (disuccinimidyl tartrate), BS(PEG)9 (PEGylated bis(sulfosuccinimidyl)suberate), BS(PEG)5 (PEGylated bis(sulfosuccinimidyl)suber ate), Dimethyl 3,3'-dithiopropionimidate, 4,4'-Di-isothiocyanatostilbene-2,2'- disulfonic acid, 3,3'-Dithiodipropionic acid di(N- hydroxysuccinimide ester), Dimethyl pimelimidate dihydrochloride, Ethylene glycol-bis(succinic acid N-hydroxysuccinimide ester), Suberic acid bis(N- hydroxysuccinimide ester), Suberic acid bis(3-sulfo-N- hydroxysuccinimide ester), and the like. |
| Sulfhydryl-to-sulfhydryl | Di Maleimides/di haloacetyl/di pyridyldithiol/di vinyl-sulfone/di alkene with radical. For example: 1,4-Bis[3-(2-pyridyldithio)propionamido]butane, BMOE (bis-maleimidoethane), BM(PEG)2 (1,8-bismaleimido-diethyleneglycol), BM(PEG)3 (1,11-bismaleimido-triethyleneglycol), DTME (dithio-bis-maleimidoethane), and the like. |
| Amine to sulfhydryl | (NHS ester, isocynanate, isothiocyanate, acid halid, or anhydride) and (maleimide, haloacetyl, pyridyldithiol, vinylsulfone, or alkene with radical) For Example: Sulfo-SMPB (sulfosuccinimidyl 4-(N-maleimido-phenyl)butyrate), Sulfo-SIAB (sulfosuccinimidyl (4-iodoacetyl)aminobenzoate), Sulfo-N-succinimidyl 4-maleimidobutyrate, Sulfo-MBS (m-maleimidobenzoyl-N-hydroxysulfosuccinimide ester), Sulfo-LC-SPDP (sulfosuccinimidyl 6-[3'-(2-pyridyl-dithio)propionamido]hexanoate), Sulfo-KMUS (N-(κ-maleimidoundecanoyloxy) sulfosuccinimide ester), Sulfo-EMCS (N-(ε-maleimidocaproyloxy) sulfosuccinimide ester), SMPT (4-succinimidyloxy-carbonyl-alpha-methyl-alpha(2-pyridyldithio)toluene), SMPH (succinimidyl-6-((b-maleimidopropion-amido)hexanoate), SM(PEG)24 (PEGylated, long-chain SMCC crosslinker), SIAB (N-succinimidyl (4-iodo-acetyl)aminobenzoate), SBAP (succinimidyl 3-(bromoacetamido)propionate), PEG4-SPDP (PEGylated, long- chain SPDP crosslinker), PEG12-SPDP (PEGylated, long-chain SPDP crosslinker), O-[N-(3- Maleimidopropionyl)aminoethyl]-O'-[3-(N-succinimidyloxy)-3-oxopropyl]tri ethylene glycol, O-[N-(3-Maleimidopropionyl)amino-ethyl]-O'-[3-(N-succinimidyloxy)-3-oxopropyl]heptacosaethylene glycol, Maleimido-acetic acid N-hydroxysuccinimide ester, Maleimide-PEG8-succinimidyl ester, Maleimide-PEG6-succinimidyl ester, Maleimide-PEG2-succinimidyl ester, Maleimide-PEG12-succinimidyl ester, LC-SPDP (succinimidyl 6-[3(2-pyridyldithio)propion-amido]hexanoate), LC-SMCC (succinimidyl-4-(N-maleimidomethyl)cyclohexane-1-carboxy-(6-amido-caproate)), Iodoacetic acid N-hydroxysuccinimide ester, Bromoacetic acid N-hydroxysuccinimide ester, 6-Maleimidohexanoic acid N-hydroxysuccinimide ester, |

-continued

| Moieties for Attachment | Activated Precursors |
|---|---|
| | 4-Maleimidobutyric acid N-hydroxysuccinimide ester, 4-(4-Maleimidophenyl)butyric acid N-hydroxysuccinimide ester, 3-Maleimidopropionic acid N-hydroxysuccinimide ester, 3-(2-Pyridyldithio)propionic acid N-hydroxy-succinimide ester, and the like. |
| Carboxyl-to-amine | Carbodiimide |
| Hydroxyl-to-sulfhydryl | Isocyanate and (maleimide, haloacetyl, pyridyldithiol, vinylsulfone, or alkene with radical) |

Methods for attachment of linkers are known in the art as chemical conjugation. A review of the art of conjugation is hereby incorporated by reference in its entirety, see Hermanson, G. T. (2013). Bioconjugate Techniques. Academic Press.

Cleavable Moieties

The disclosure provides cleavable moieties which include cleavable protecting groups. In exemplary embodiments, the cleavable moiety includes a protective group, a linker or a linker lengthening moiety. In some embodiments, the protective group, the linker or the linker lengthening moiety may be attached to a detectable moiety, including but not limited to a fluorescent moiety or a fluorophore known to those of skill in the art. The cleavable moiety may be attached to the nucleobase or the 3'-OH of the pentose of the nucleotide molecule to terminate enzymatic polynucleotide extension (primer extension). As used herein exemplary 3'-OH protecting groups may be ethers, esters, carbonates, carbamates or silyl ethers, or their derivatives. Exemplary protecting groups or linkers may have a fluorophore moiety attached thereto. Cleavable moieties may be cleaved in a variety of conditions, for example, the moieties may be photocleavable, thermo-cleavable, electrochemically cleavable, transition metal cleavable or pH cleavable. Linker lengthening moiety may include any moiety known to one skilled in the art that can be appropriately functionalized to provide tuned distance and rigidity between the protective or linker group and the detectable moiety.

Exemplary cleavable protecting groups or linkers are described in Leriche, G., Chisholm, L., & Wagner, A., (2012), Cleavable linkers in chemical biology, Bioorganic and Medicinal Chemistry, 20(2), 571-582 hereby incorporated by reference in its entirety. It is to be understood that cleavable protecting groups are known to those of skill in the art and can be readily identified by literature search.

The following examples are set forth as being representative of the present disclosure. These examples are not to be construed as limiting the scope of the present disclosure as these and other equivalent embodiments will be apparent in view of the present disclosure, figures and accompanying claims.

Example I

Figure 2:
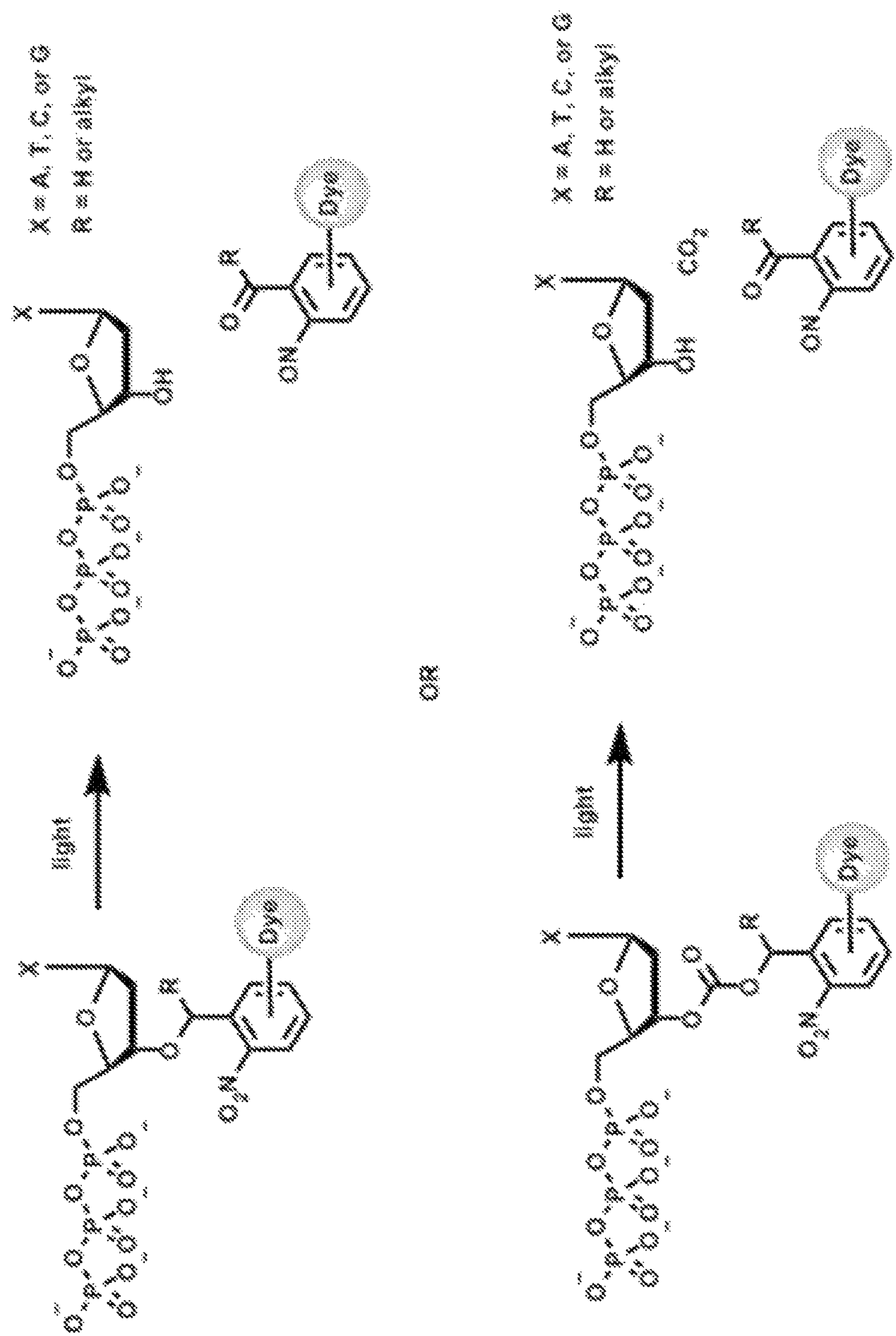
FIG. 2 depicts general structures and cleavage products of exemplary nucleotides.

In certain embodiments of the present disclosure, the cleavable moiety is photocleavable, and will be cleaved in certain wavelengths of light. In one embodiment of the disclosure, the nucleotides are ortho-nitrobenzyl modified 3' hydroxy nucleotide polyphosphates. FIG. 2 depicts general structures and cleavage products of the exemplary nucleotides. Structures are shown for both ether and carbonate linkages. UV light may be used for cleavage of ortho-nitrobenzyl ether and carbonate derivatives, for example at 365 nm wavelengths of light.

Figure 3:
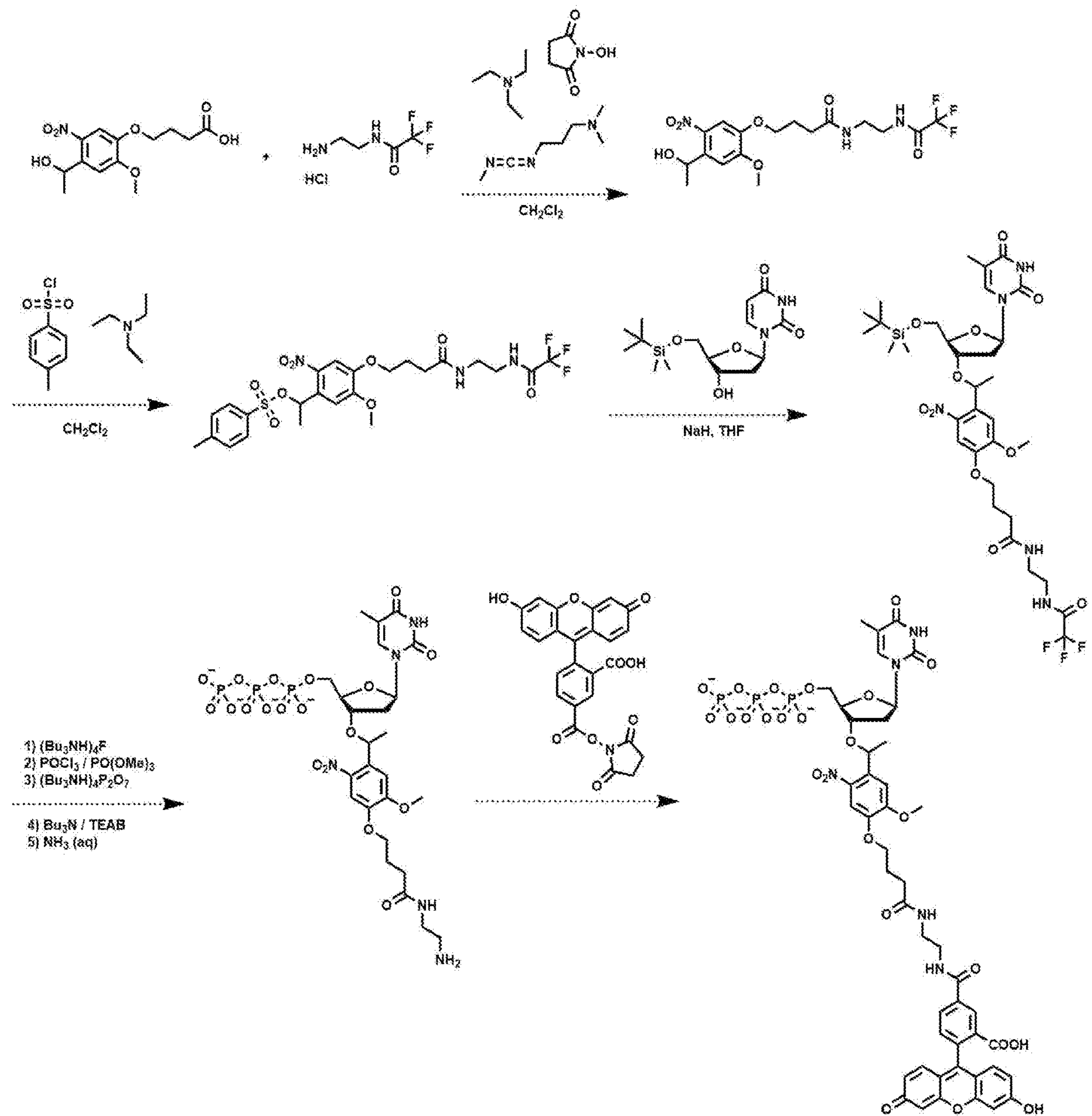
FIG. 3 depicts an exemplary synthesis procedure for an exemplary target.

The nucleotide analogs of the present disclosure are synthesized by a number of procedures. An exemplary synthesis procedure for an exemplary target is shown in FIG. 3. An exemplary synthesis procedure for a second exemplary target is shown in FIG. 4.

Figure 4:
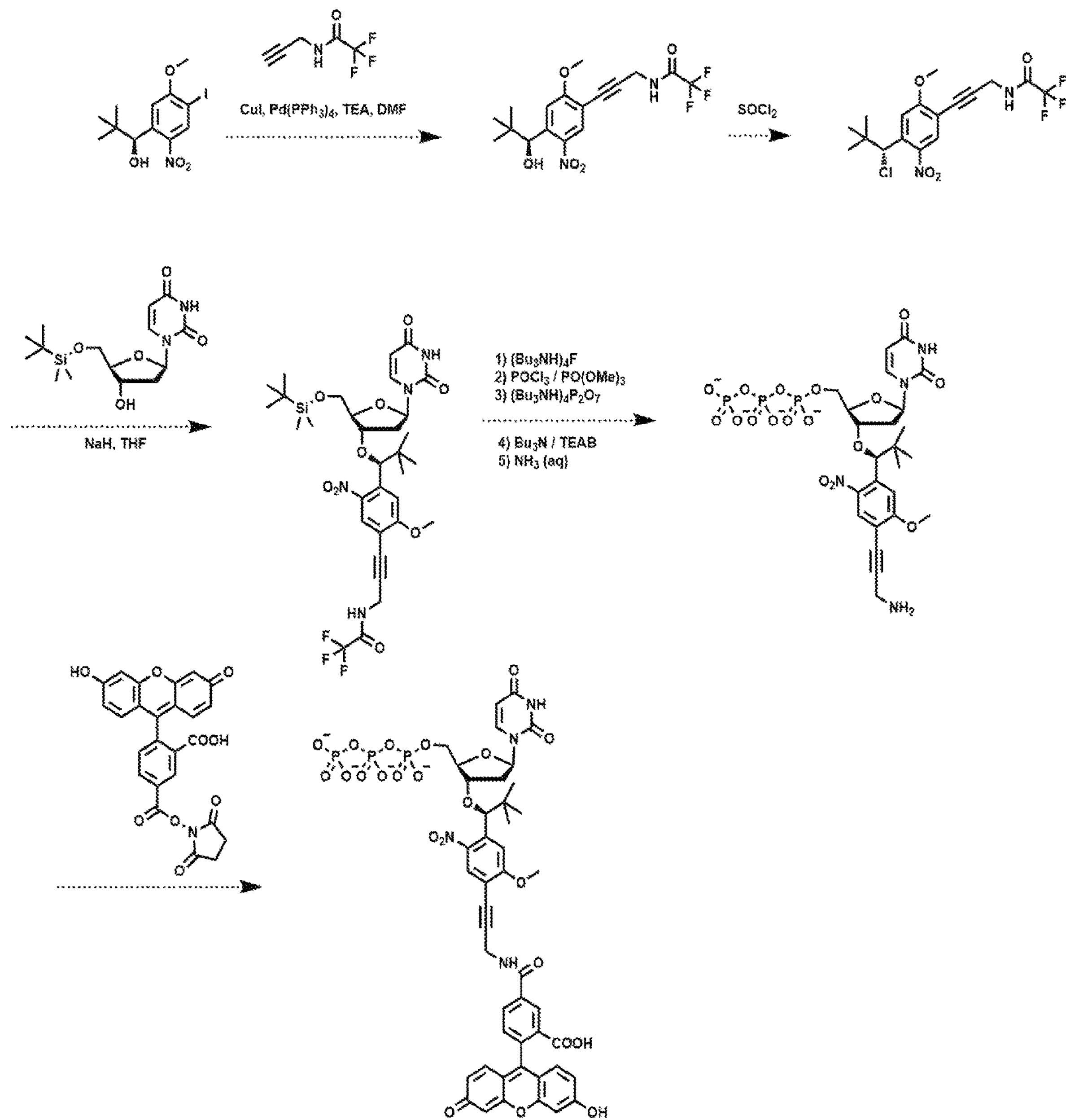
FIG. 4 depicts an exemplary synthesis procedure for a second exemplary target.

In an exemplary embodiment, the starting material for the synthesis procedure of FIG. 4 is (S)-1-(4-Iodo-5-methoxy-2-nitrophenyl)-2,2-dimethylpropan-1-ol of the structure:

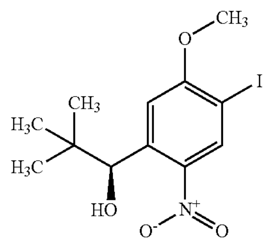 [SMILES: COc1cc([C@@H](O)C(C)(C)C)c([N+](=O)[O-])cc1I]

Figure 5:
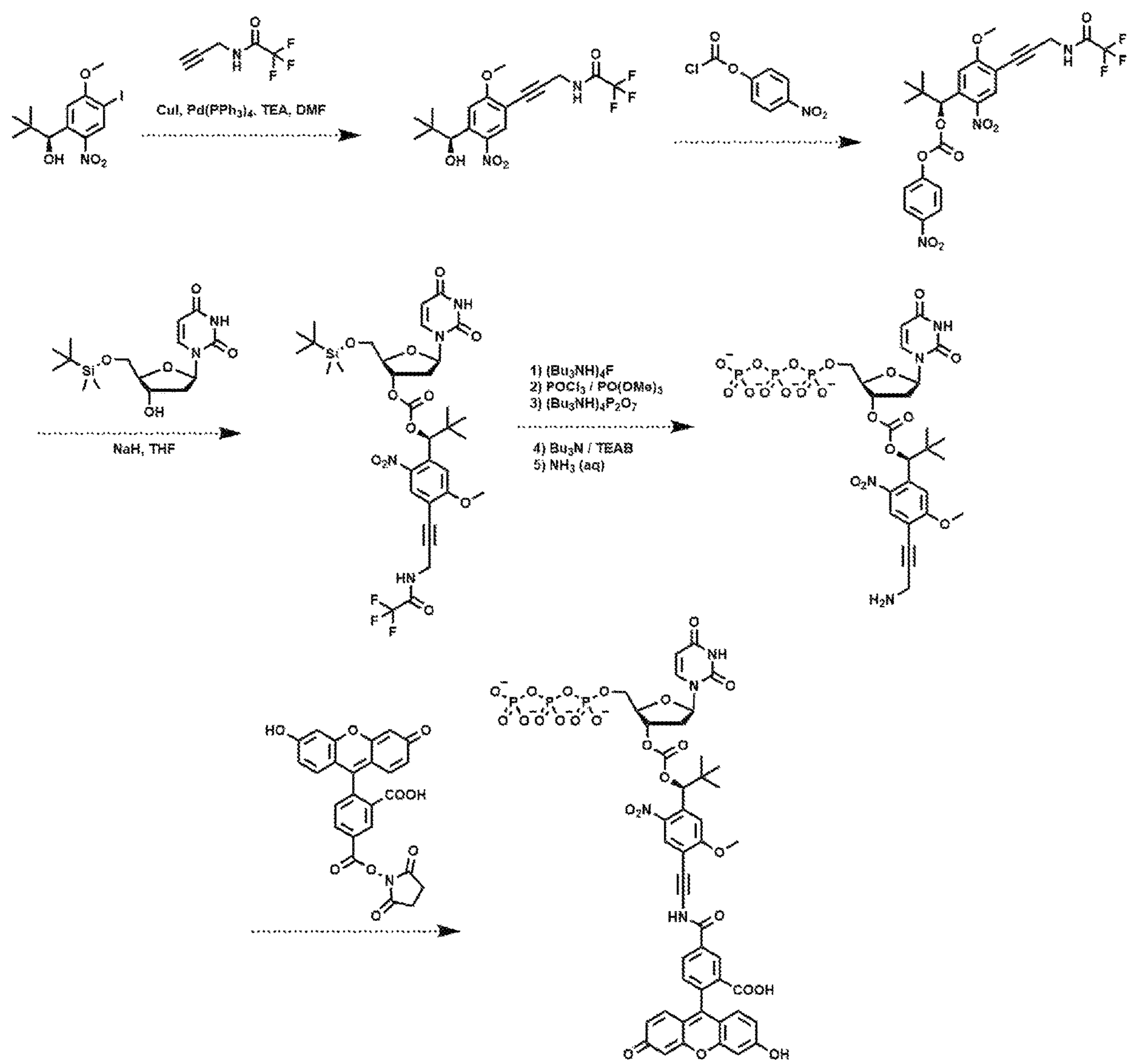
FIG. 5 depicts an exemplary synthesis procedure for a third exemplary target.

An exemplary synthesis procedure for a third exemplary target is shown in FIG. 5. In an exemplary embodiment, the starting material for the synthesis procedure of FIG. 5 is (S)-1-(4-Iodo-5-methoxy-2-nitrophenyl)-2,2-dimethylpropan-1-ol of the structure:

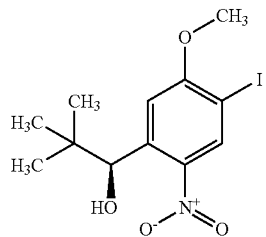 [SMILES: COc1cc([C@@H](O)C(C)(C)C)c([N+](=O)[O-])cc1I]

Figure 6:
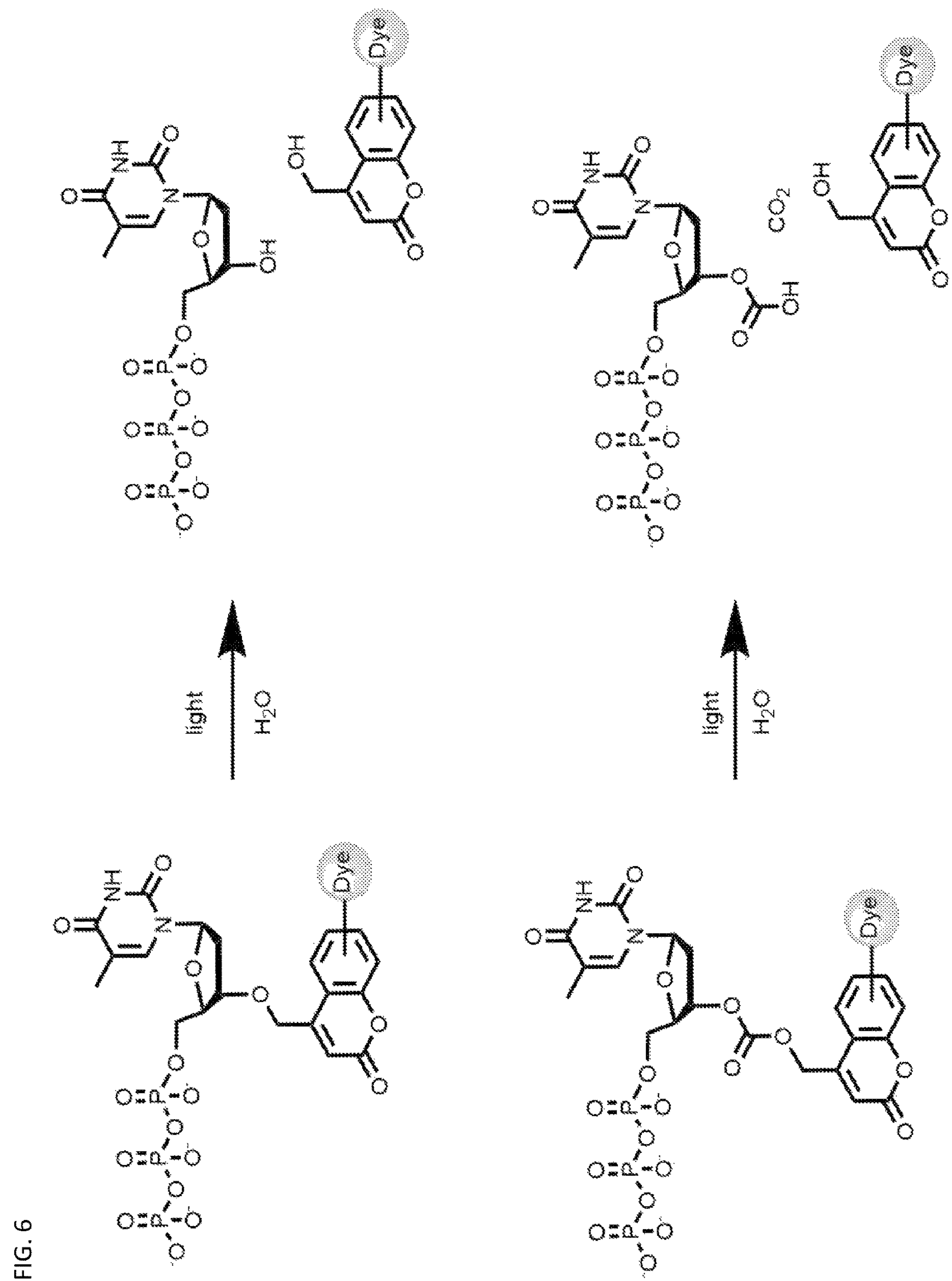
FIG. 6 depicts general structures and cleavage products of exemplary nucleotides.

In another embodiment of the invention, the nucleotides are coumarin modified at the 3' hydroxy nucleotide polyphosphates. FIG. 6 depicts general structures and cleavage products of exemplary nucleotides. Structures are shown for both ether and carbonate linkages. UV light may be used for cleavage of the coumarin ether and carbonate derivatives, for example 400 nm light. Photocleavable linkers are known in the art and described in Chem. Rev. 2013, 113, 119-191, hereby incorporated by reference in its entirety.

The nucleotide analogs of the present disclosure are synthesized by a number of procedures.

Figure 7:
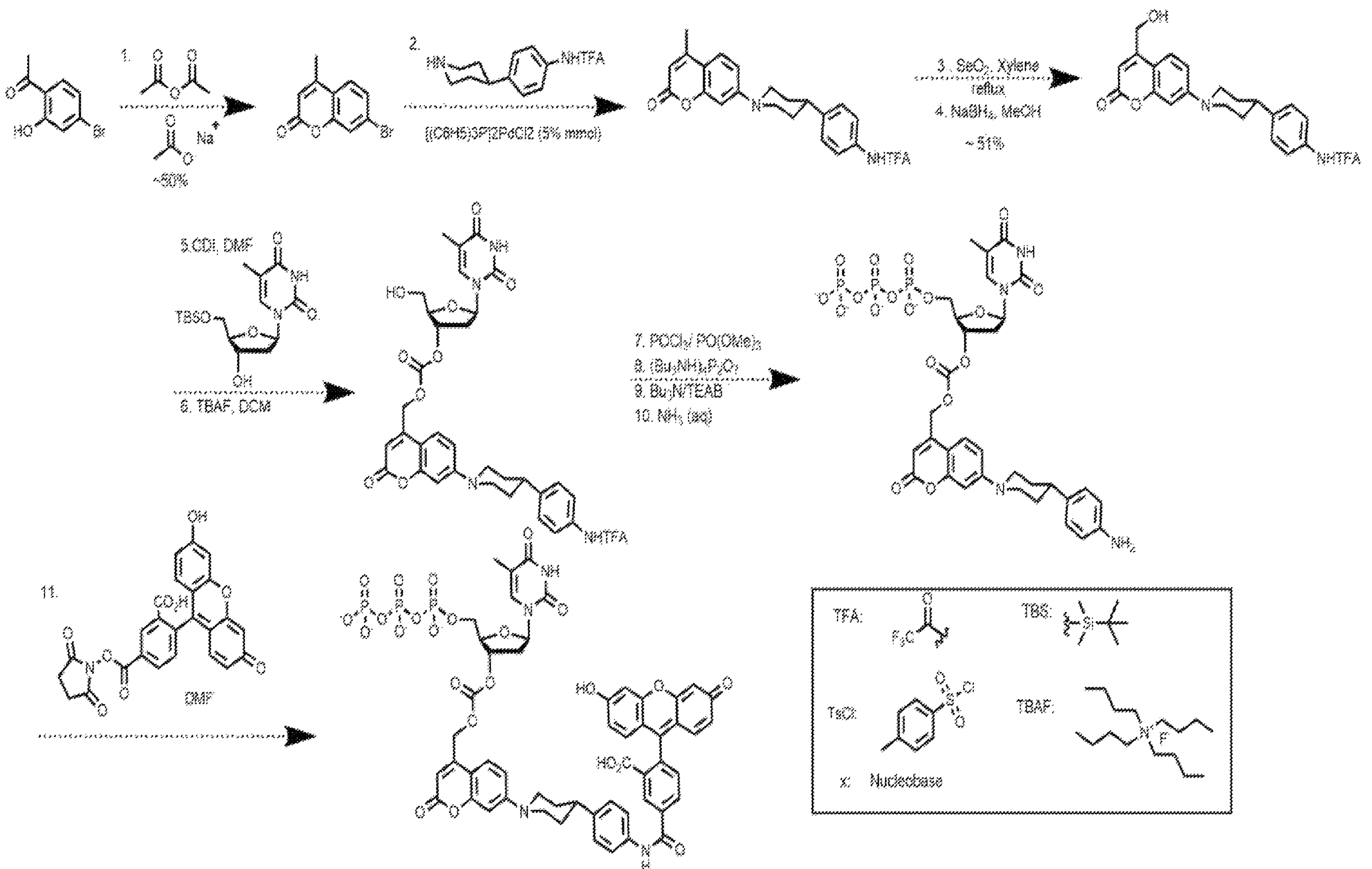
FIG. 7 depicts an exemplary synthesis procedure for an exemplary target.

An exemplary synthesis procedure for an exemplary target is shown in FIG. 7. For reaction 1, see reference: dx.doi.org/10.1021/jm400637m; J. Med. Chem. 2013, 56, 7516-7526, hereby incorporated by reference in its entirety. For reaction 2, see the following references: Tetrahedron Letters 41 (2000) 9957-9961 (for the preparation of the amine) and DOI: 10.1021/jacs.6b03924; J. Am. Chem. Soc. 2016, 138, 6960-6963 (For the coupling) hereby incorporated by reference in their entireties. For reaction 3, see Chem. Commun., 2014, 50, 1256-1258; DOI: 10.1039/c3cc48263d, hereby incorporated by reference in its entirety.

In an exemplary embodiment, the starting material for the synthesis procedure of FIG. 7 1-(4-bromo-2-hydroxyphenyl)ethan-1-one of the structure:

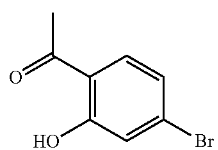

Figure 8:
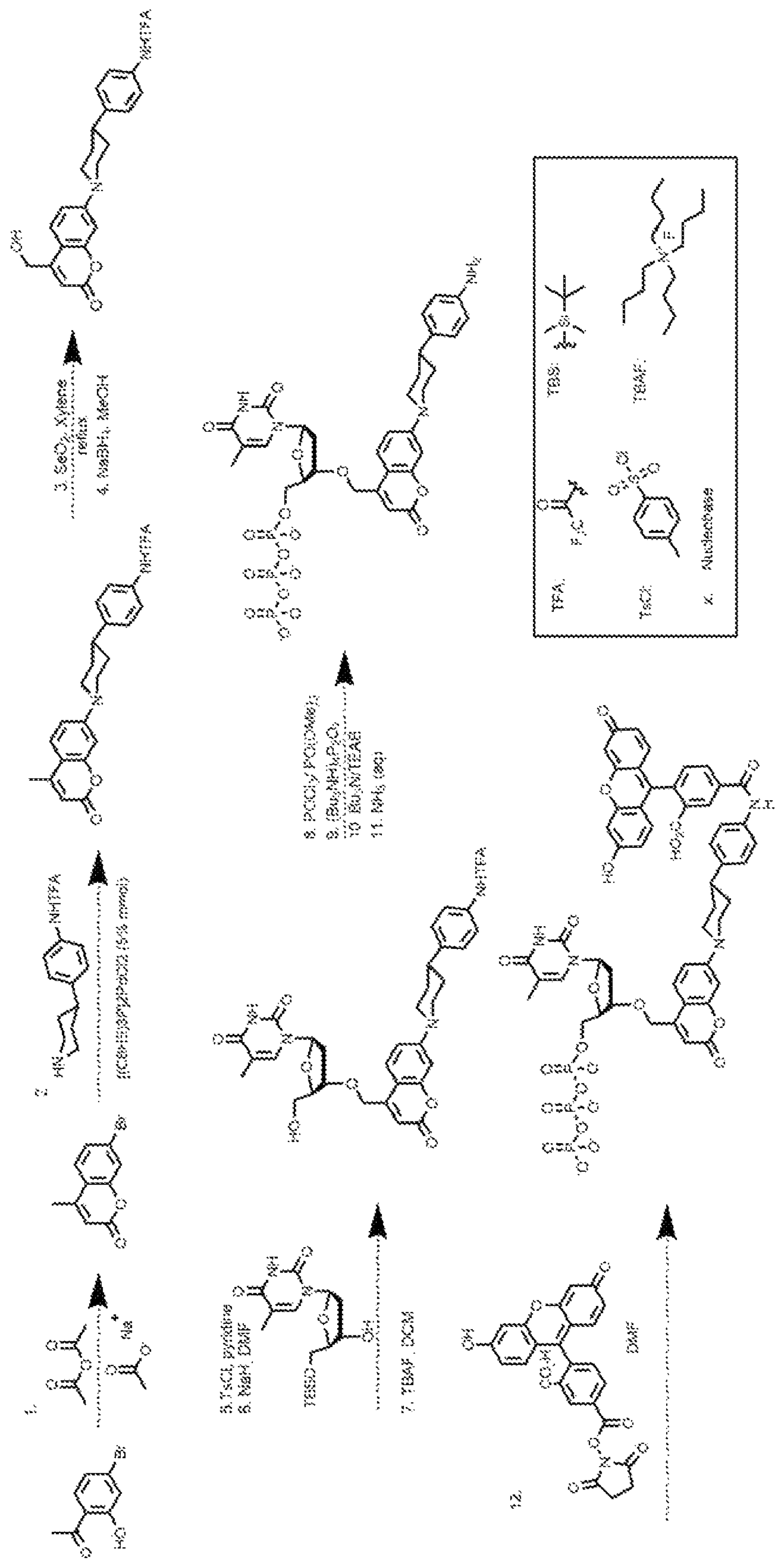
FIG. 8 depicts an exemplary synthesis procedure for a second exemplary coumarin target.

An exemplary synthesis procedure for a second exemplary coumarin target is shown in FIG. 8. For reaction 1, see reference: dx.doi.org/10.1021/jm400637m; J. Med. Chem. 2013, 56, 7516-7526, hereby incorporated by reference in its entirety. For reaction 2, see the following references: Tetrahedron Letters 41 (2000) 9957-9961 (for the preparation of the amine) and DOI: 10.1021/jacs.6b03924; J. Am. Chem. Soc. 2016, 138, 6960-6963 (For the coupling), hereby incorporated by reference in their entireties. For reaction 3, see Chem. Commun., 2014, 50, 1256-1258; DOI: 10.1039/c3cc48263d, hereby incorporated by reference in its entirety.

In an exemplary embodiment, the starting material for the synthesis procedure of FIG. 8 is 1-(4-bromo-2-hydroxyphenyl)ethan-1-one of the structure:

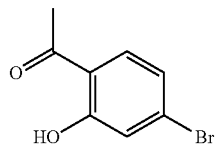

Figure 9:
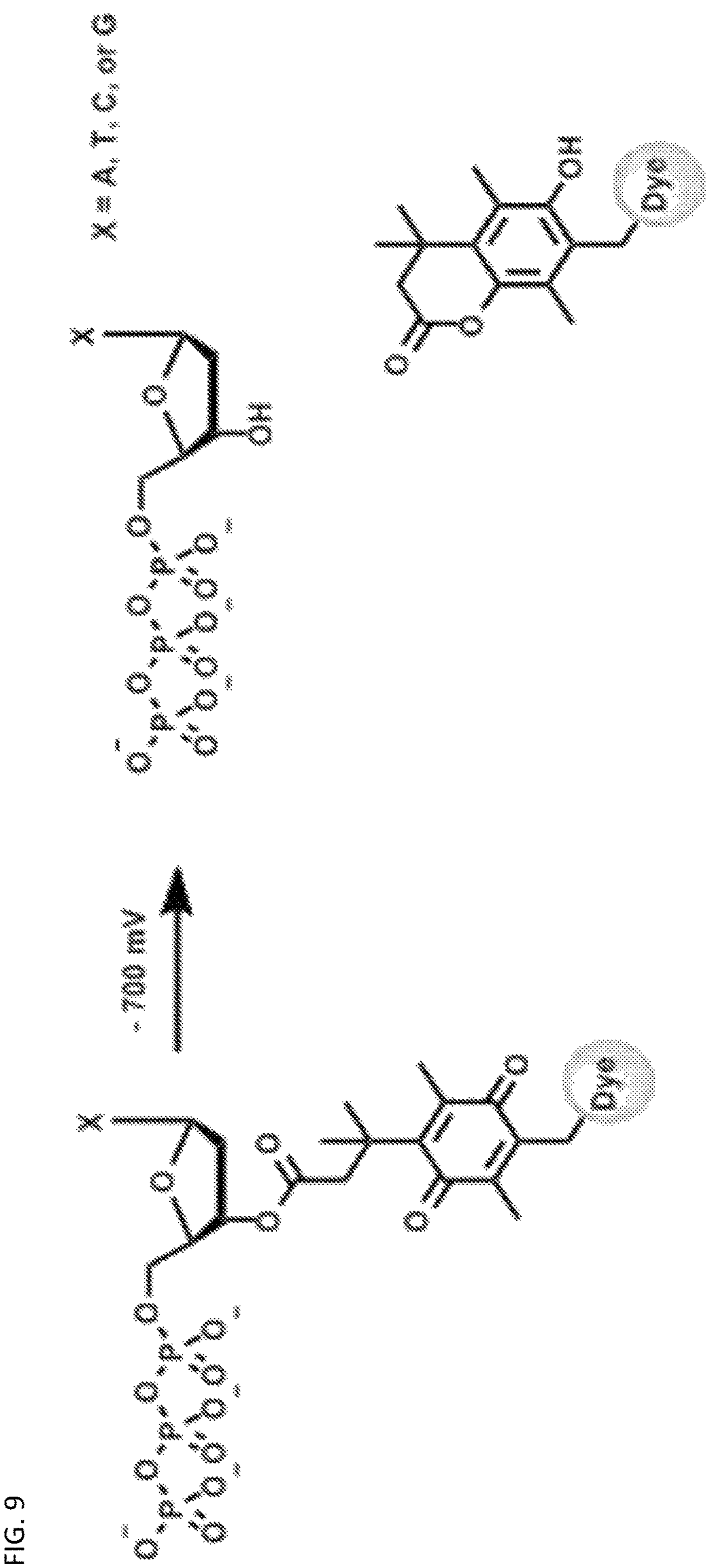
FIG. 9 depicts a general structure and the electrochemical cleavage product of quinone modified 3' hydroxy nucleotide polyphosphates.

According to certain embodiments of the present disclosure, the cleavable moiety is electrochemically cleavable, and will be cleaved at certain oxidizing or reducing potentials. Oxidizing or reducing potentials can be provided by reagents such as reducing or oxidizing agents, or by an electrode. In an exemplary embodiment of the electrochemically cleavable nucleotide triphosphates, the cleavable moiety is a quinone. FIG. 9 depicts a general structure and the electrochemical cleavage product of quinone modified 3' hydroxy nucleotide polyphosphates. Synthesis of the quinone is described in J. Org. Chem. 1999, 64, 156-161, hereby incorporated by reference in its entirety.

Figure 10:
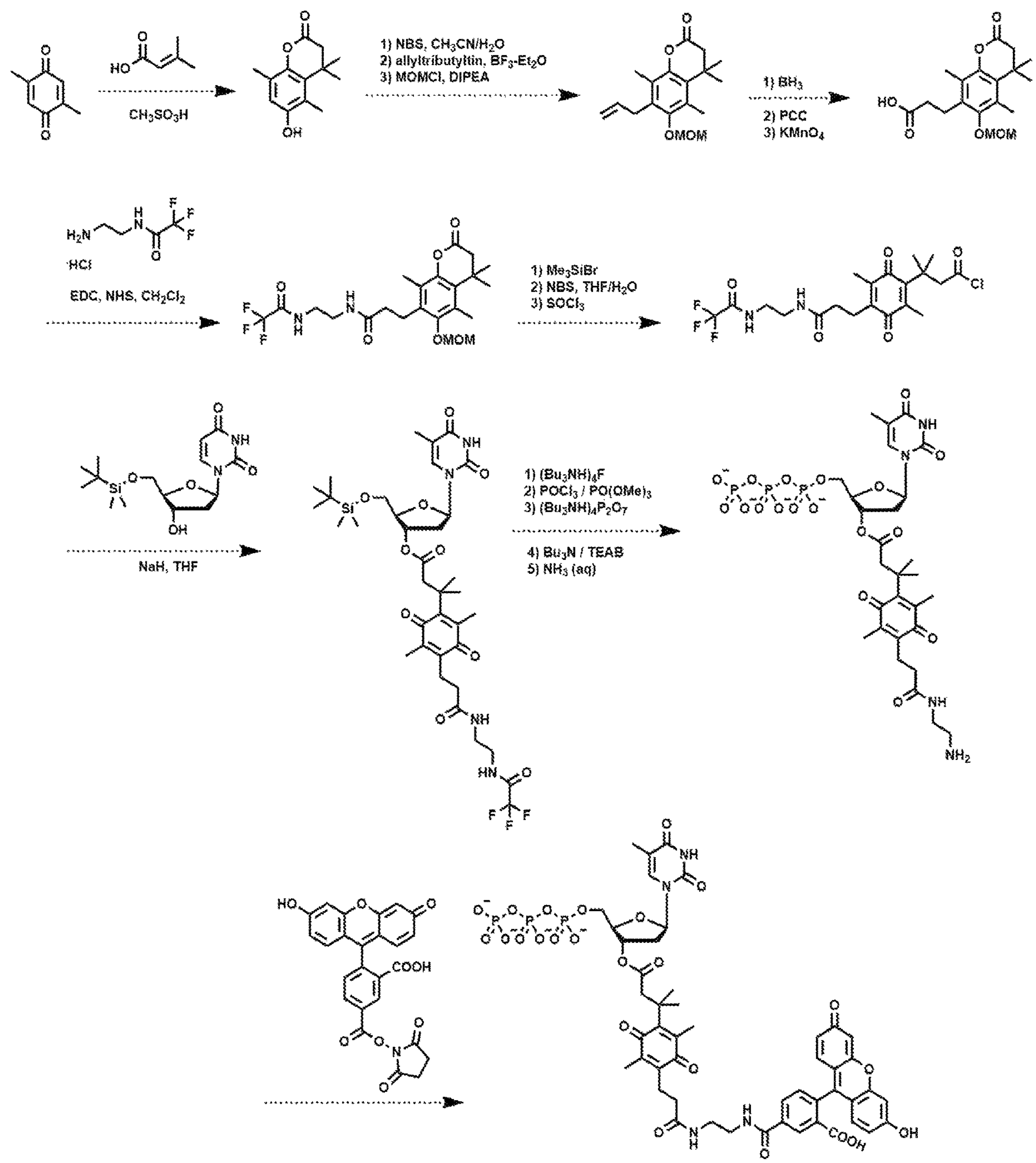
FIG. 10 depicts an exemplary synthesis procedure for an exemplary target of a quinone cleavable group.
Figure 11:
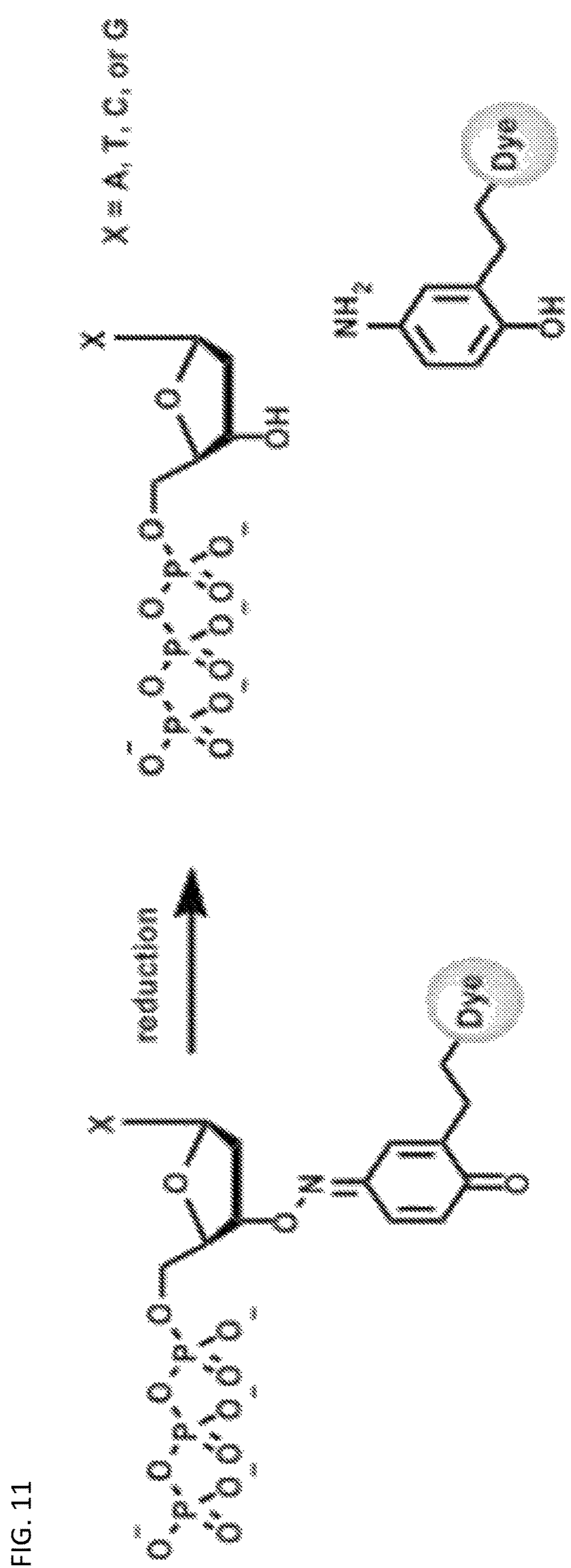
FIG. 11 depicts a general structure and cleavage product of an alternative modified 3' hydroxy nucleotide polyphosphates which can be cleaved electrochemically.
Figure 12:
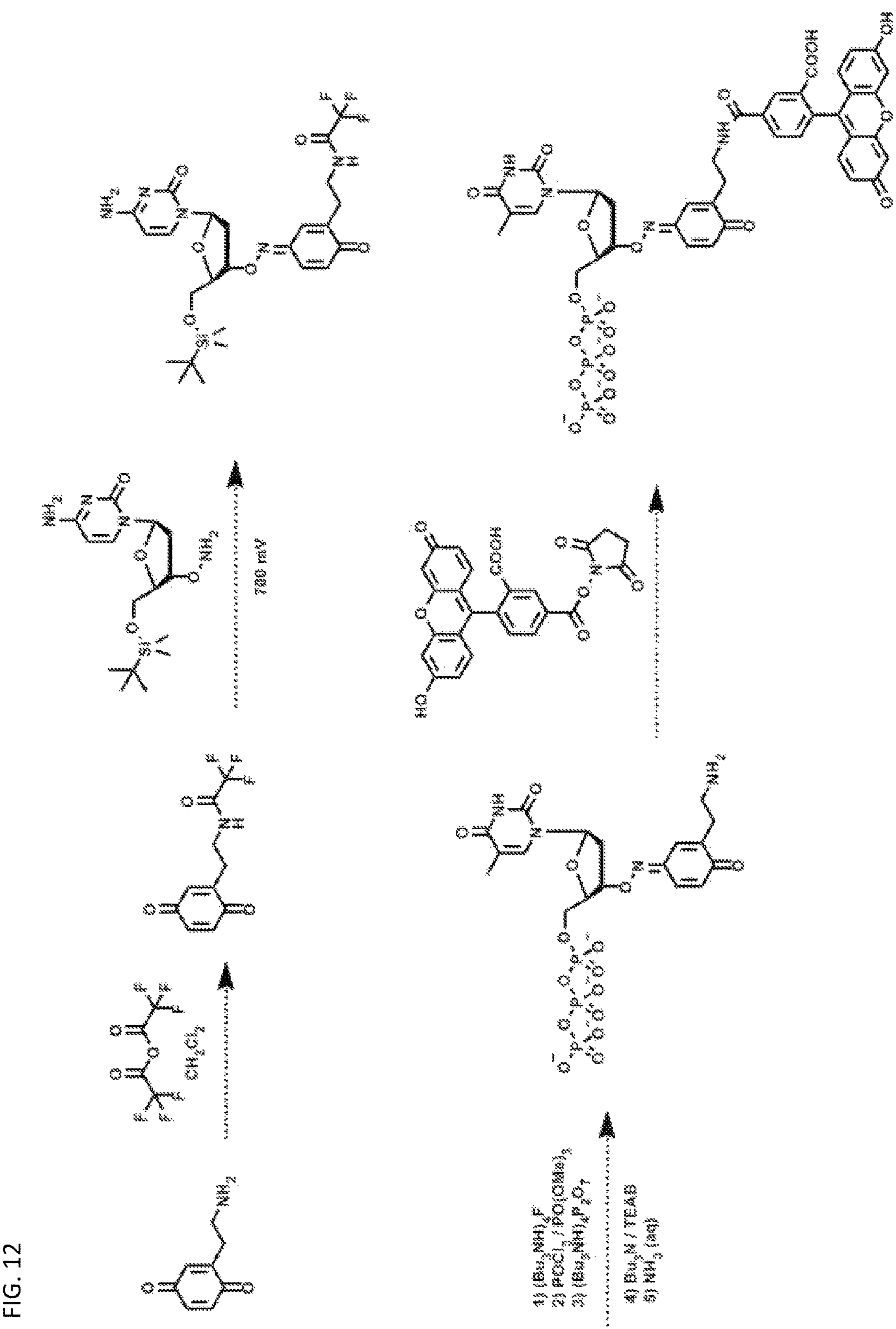
FIG. 12 depicts an exemplary synthesis procedure for an exemplary target.

An exemplary synthesis procedure for an exemplary target of a quinone cleavable group is shown in FIG. 10. FIG. 11 depicts a general structure and cleavage product of an alternative modified 3' hydroxy nucleotide polyphosphates which can be cleaved electrochemically. An exemplary synthesis procedure for an exemplary target is shown in FIG. 12.

Figure 13:
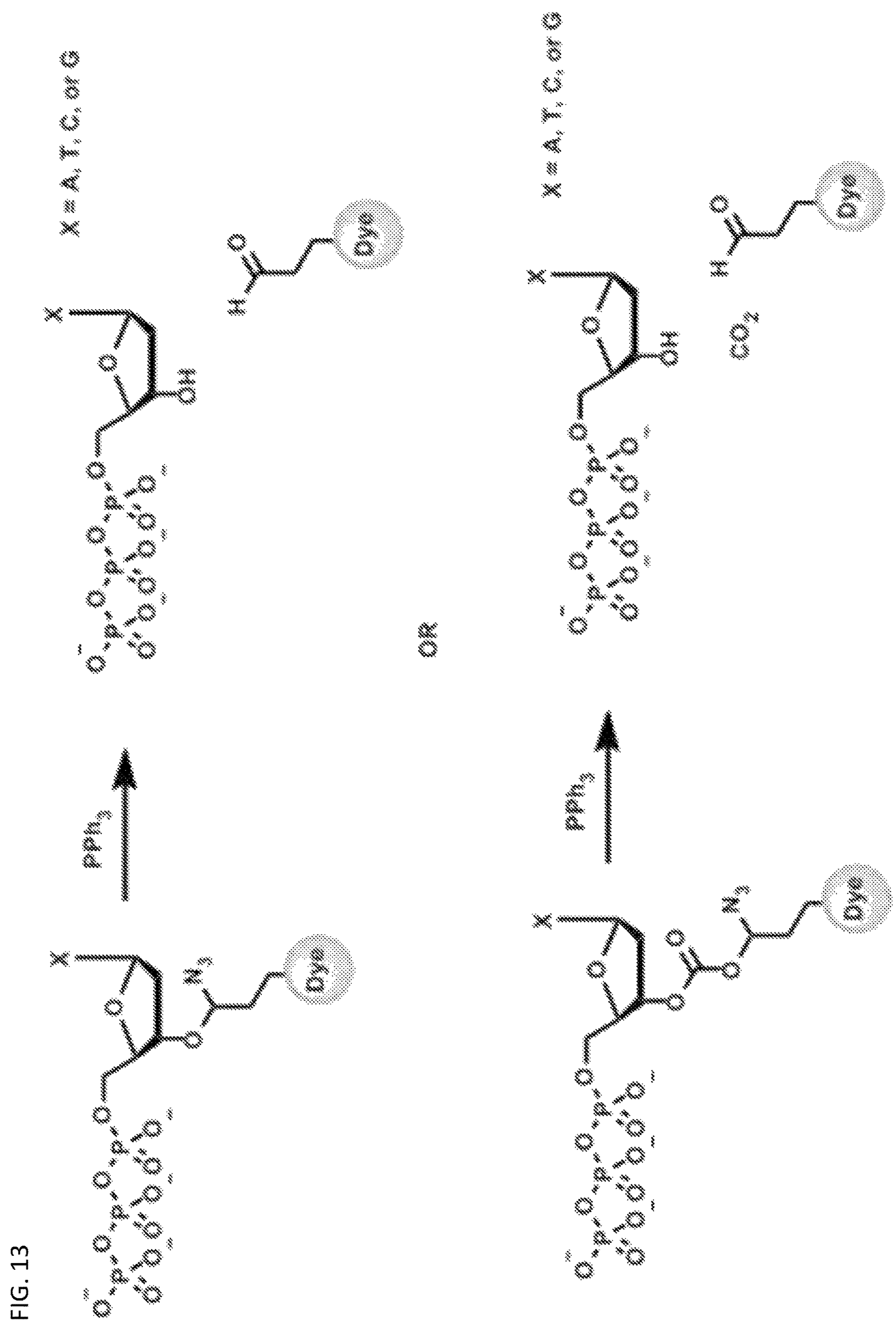
FIG. 13 depicts a general structure and cleavage product of azidomethylene modified 3' hydroxy nucleotide polyphosphates which can be cleaved with a reducing agent such as a phosphine.
Figure 14:
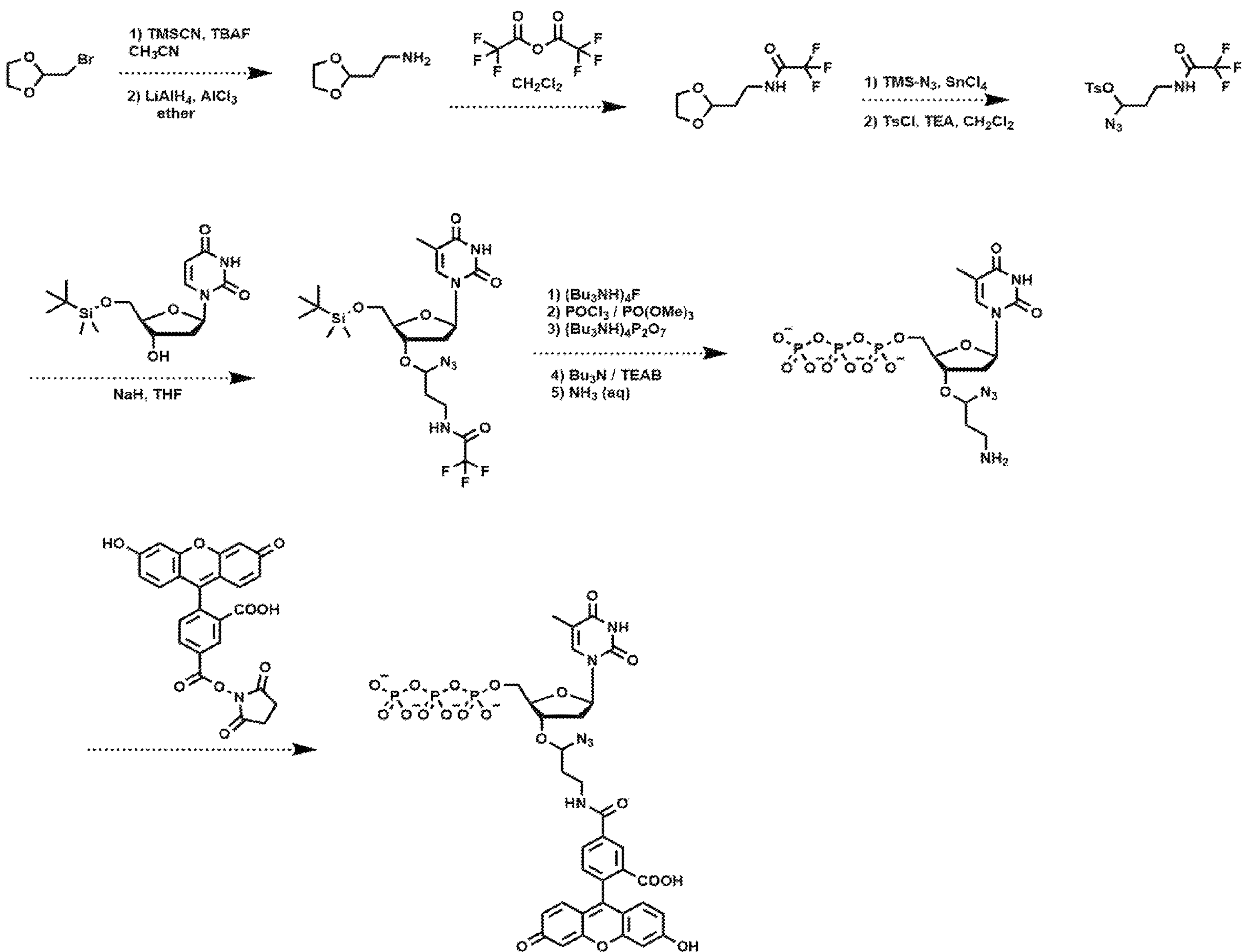
FIG. 14 depicts an exemplary synthesis procedure for an exemplary target.

According to other aspects of the disclosure, the electrochemically cleavable group is an azidomethylene derivative. FIG. 13 depicts a general structure and cleavage product of azidomethylene modified 3' hydroxy nucleotide polyphosphates which can be cleaved with a reducing agent such as a phosphine. Synthesis of the azidomethyene linker is described in Nature 2008, 456, 53-59, hereby incorporated by reference in its entirety. An exemplary synthesis procedure for an exemplary target is shown in FIG. 14.

Figure 15:
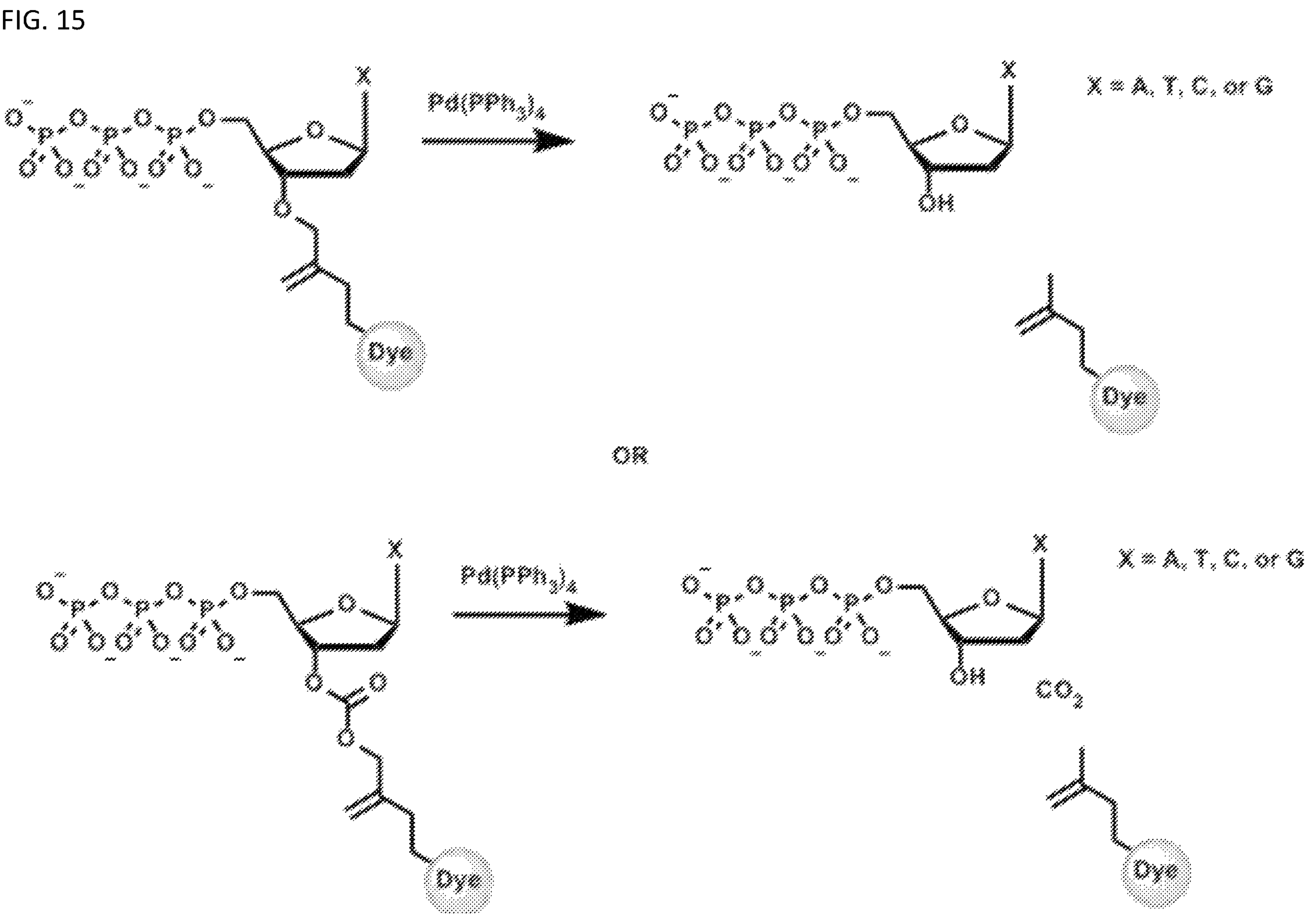
FIG. 15 depicts a general structure and cleavage product of allyl modified 3' hydroxyl nucleotide polyphosphates which can be cleaved with palladium.
Figure 16:
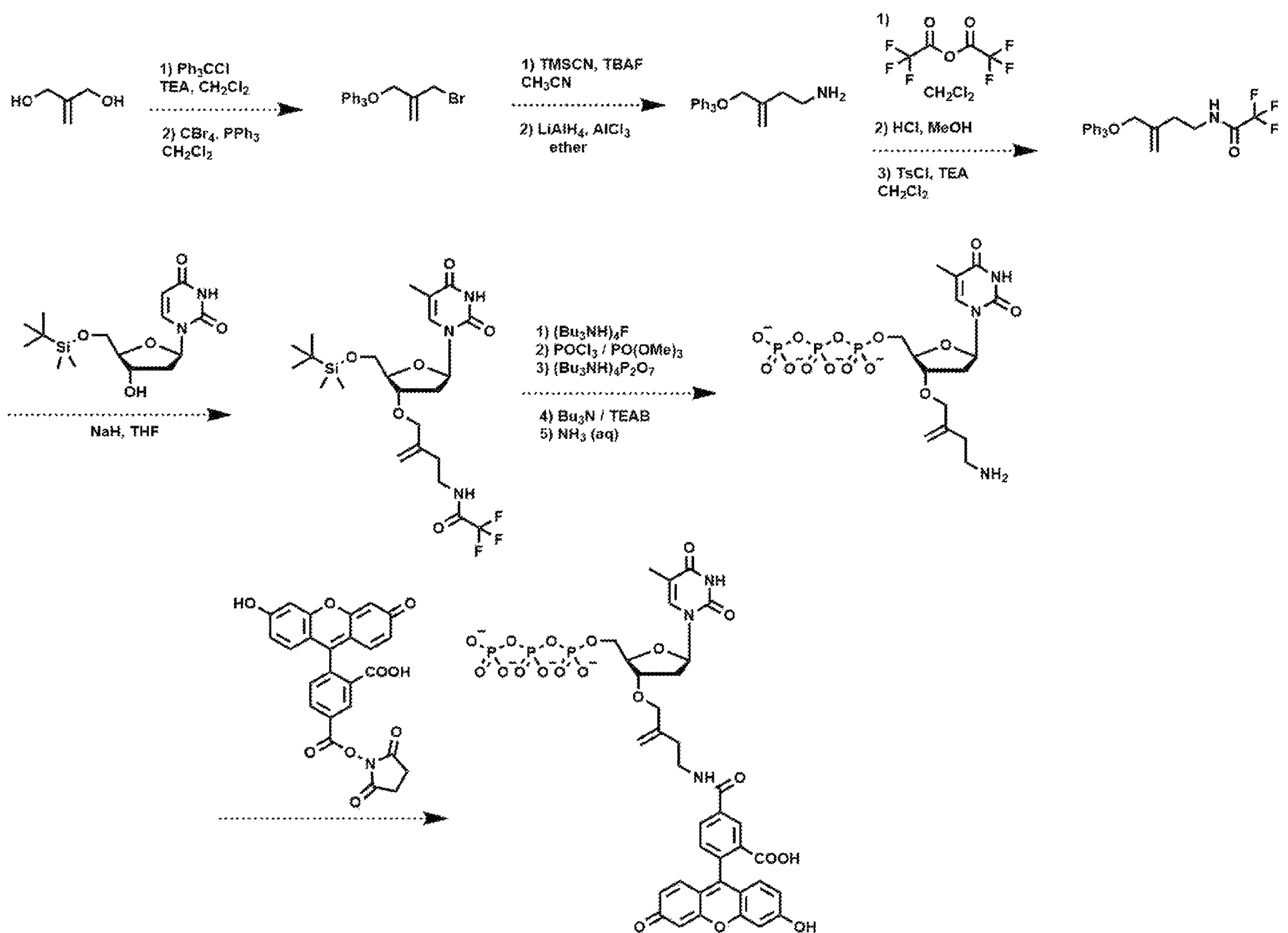
FIG. 16 depicts an exemplary synthesis procedure for an exemplary target.

In certain embodiments of the present disclosure, the 3'-OH protection group is a transition metal cleavable moiety. Suitable transition metals for cleavage may include palladium, platinum, ruthenium or other transition metals. FIG. 15 depicts a general structure and cleavage product of allyl modified 3' hydroxyl nucleotide polyphosphates which can be cleaved with palladium. Structures are shown for both ether and carbonate linkages. Synthesis of the allyl linker is described in PNAS. 2006, 103, 19635-19640, hereby incorporated by reference in its entirety. An exemplary synthesis procedure for an exemplary target is shown in FIG. 16.

Figure 17:
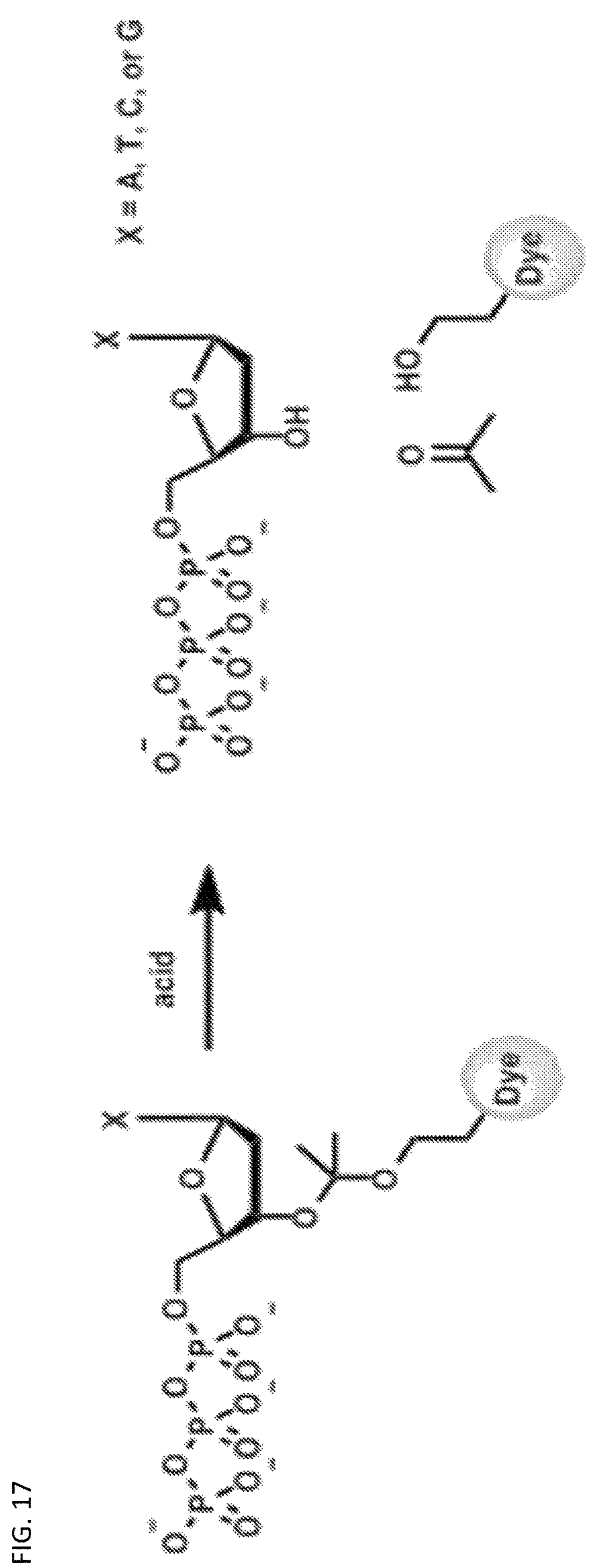
FIG. 17 depicts a general structure and cleavage product of ketal modified 3' hydroxy nucleotide polyphosphates which can be cleaved with acidic conditions, such as in the presence of polyphosphines.
Figure 18:
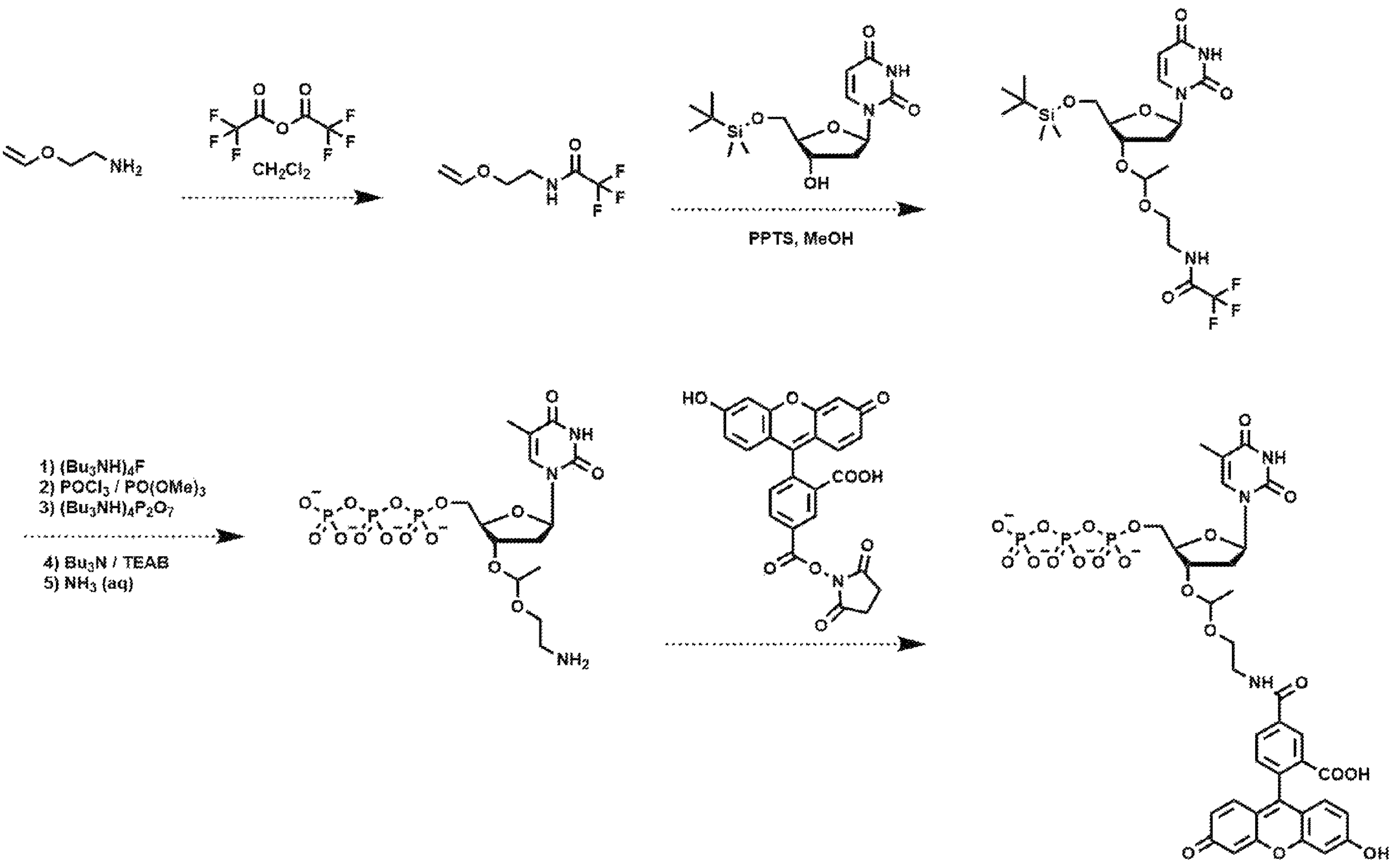
FIG. 18 depicts an exemplary synthesis procedure for an exemplary target.

In certain embodiments of the disclosure, the cleavable moiety is acid cleavable. FIG. 17 depicts a general structure and cleavage product of ketal modified 3' hydroxy nucleotide polyphosphates which can be cleaved with acidic conditions, such as in the presence of polyphosphines. Synthesis of the acetal linker is described in Bioconjugate Chem., 2008, 19, 876-881, hereby incorporated by reference in its entirety. An exemplary synthesis procedure for an exemplary target is shown in FIG. 18.

Nucleotide analogs of the present disclosure are not limited to the exemplary nucleotides, and may contain any combination of the provided cleavable moieties, fluorophores and linkers.

Example II

Figure 19:
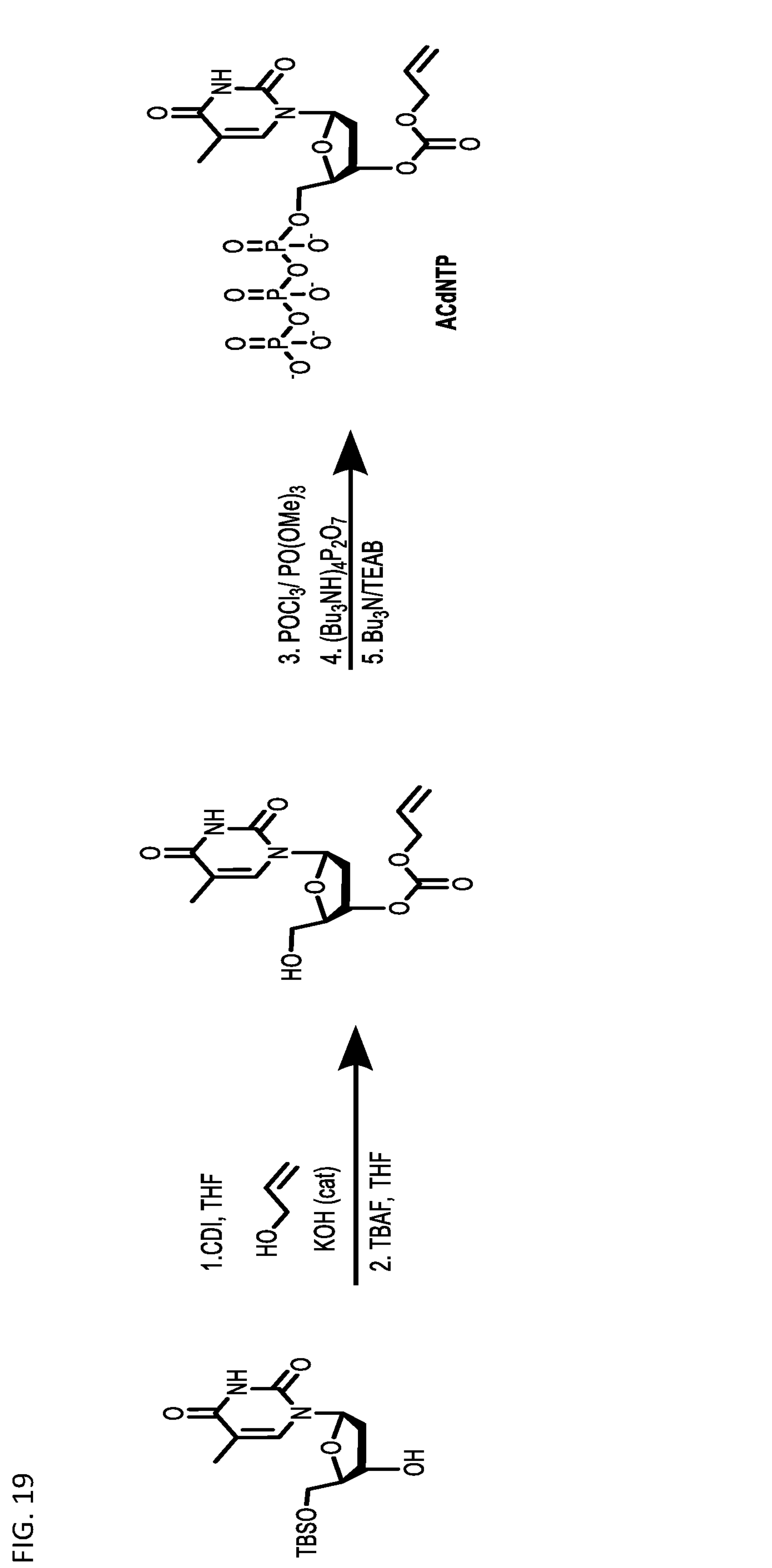
FIG. 19 depicts a synthesis reaction for allyl carbonate dNTP (ACdNTP).

3'-Allyl carbonate dNTP (ACdNTP) was prepared as follows and as shown in FIG. 19 using the following steps 1-5.

Step 1: Under a blanket of argon at room temperature, carbonyldiimidazole ("CDI" circa 1.2 eq) was added to a stirring solution of TBS protected thymidine (1 eq.) in THF (0.1 M reaction concentration). Catalytic KOH (circa 0.2 eq) was then added. The reaction was allowed to continue until TLC indicates consumption of substrate. In some instances, additional portions of CDI may be needed to completely consume starting material.) At this point, allyl alcohol (1.2 eq) was added in one portion. Once the reaction was complete as indicated by TLC, the reaction was stopped with the addition of water. The product was then extracted with ethyl acetate. Washing with brine and drying over sodium sulfate provided the crude product. Purification by column chromatography (stationary phase of silica gel and mobile phase of ethyl acetate: hexane) provided the desired product, which is the 5'-TBS-3'-allyl carbonate thymidine.

Step 2: To the 5'-TBS-3'-allyl carbonate thymidine (1 eq) was added THF (0.1 M reaction concentration) and TBAF (1M, 1.2 eq) at room temperature. The reaction was allowed to continue until TLC indicated consumption of starting material. The reaction was stopped with the addition of water. The product was extracted with ethyl acetate. Washing with brine and drying over sodium sulfate provided the crude product, which is the 3'-allyl carbonate thymidine. Generally, purification by column chromatography (stationary phase of silica gel and mobile phase of ethyl acetate: hexane) is best practice to obtain the pure product.

Step 3: After drying over desiccant, the 3'-allyl carbonate thymidine (1 eq) was diluted with $POMe_3$ (circa. 0.06 M reaction concentration). The solution was then cooled to 0° C. Fresh $POCl_3$ (2 eq) is added slowly and the reaction is allowed to continue at 0° C. for 1 to 3 hours. See Chem. Rev. 2016, 116, 7854-789; Acta Biochim. Biophys. Acad. Sci. Hung. 1981, 16 (3-4), 131-133; and Yoshikawa, M.; Kato, T.; Takenishi, T. A Novel Method for Phosphorylation of Nucleosides to 5'-Nucleotides. Tetrahedron Lett. 1967, 8 (50), 5065-5068 each of which is hereby incorporated by reference in its entirety.

Step 4: At 0° C., tributylammonium pyrophosphate (0.6 M, 20 eq) was added and the reaction was allowed to stir for about one to five minutes.

Step 5: The solution was then diluted with TEAB (triethylammonium bicarbonate buffer 1.0 M, pH 8.5±0.1, circa 500 mL/mmol substrate) and allowed to stir for about 12 hours. The resulting solution was washed with ethyl acetate and concentrated in vacuo. The crude product was then collected from reverse phase HPLC (acetonitrile:water, 0.1 TFA or TEAA, 5μ C18). The desired fractions were lyophilized to provide the desired 3'-allyl carbonate dNTP (ACdNTP) powder. ESI-MS m/z $(M+H)^+$ Calcd for $[C14H22N2O16P3]^+$=567.0, Found 567.0.

Example III

Figure 20:
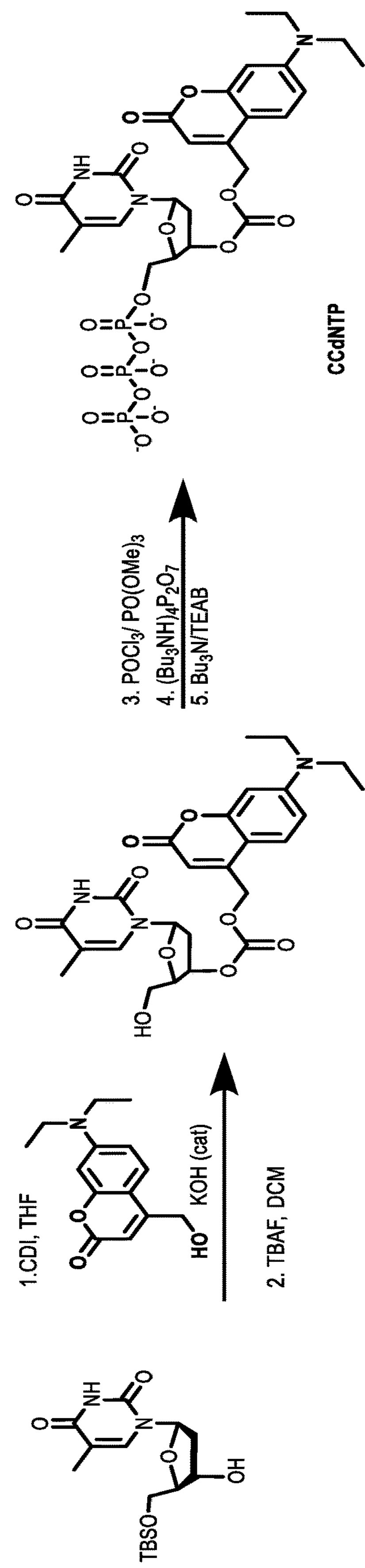
FIG. 20 depicts a synthesis reaction for coumarinyl carbonate dNTP (CCdNTP).

3'-Couraminyl carbonate dNTP (CCdNTP) was prepared as follows and as shown in FIG. 20 using the following steps 1-5.

Step 1: Under a blanket of argon at room temperature, carbonyldiimidazole ("CDI" circa 1.2 eq) was added to a stirring solution of TBS protected thymidine (1 eq.) in THF (0.1 M reaction concentration). Catalytic KOH (circa 0.2 eq) was then added. The reaction was allowed to continue until TLC indicates consumption of substrate. In some instances, additional portions of CDI may be needed to completely consume starting material. At this point, 7-(diethylamino)-4-(hydroxymethyl)-2H-chromen-2-one (1.2 eq.) was added in one portion. The reaction was stopped with the addition of water and the product was extracted with ethyl acetate. Washing with brine and drying over sodium sulfate provided the crude product. Purification by column chromatography (stationary phase of silica gel and mobile phase of ethyl acetate: hexane) provided the desired product, which is the 5'-TBS-3'-coumarinyl carbonate thymidine.

Step 2: To the 5'-TBS-3'-coumarinyl carbonate thymidine (1 eq) was added THF (0.1M reaction concentration) and TBAF (1M, 1.2 eq) at room temperature. The reaction was allowed to continue until TLC indicated consumption of starting material. The reaction was stopped with the addition of water. The product was extracted with ethyl acetate. Washing with brine and drying over sodium sulfate provided the crude product, which is the 3'-coumarinyl carbonate thymidine. Generally, purification by preparatory TLC is best practice to obtain the pure product. 3'-coumarinyl carbonate thymidine degraded when exposed to ambient and UV light for prolonged periods.

Step 3: After drying over desiccant, the 3'-coumarinyl carbonate thymidine (1 eq) was diluted with $POMe_3$ (circa. 0.06 M reaction concentration). The solution was then cooled to 0° C. Fresh $POCl_3$ (2 eq) was added slowly and the reaction was allowed to continue at 0° C. for 1 to 3 hours. See Chem. Rev. 2016, 116, 7854-789; Acta Biochim. Biophys. Acad. Sci. Hung. 1981, 16 (3-4), 131-133; and Yoshikawa, M.; Kato, T.; Takenishi, T. A Novel Method for Phosphorylation of Nucleosides to 5'-Nucleotides. Tetrahedron Lett. 1967, 8 (50), 5065-5068 each of which is hereby incorporated by reference in its entirety.

Step 4: At 0° C., tributylammonium pyrophosphate (0.6 M, 20 eq) was added and the reaction was allowed to stir for about one to five minutes.

Step 5: The solution was then diluted with TEAB (triethylammonium bicarbonate buffer 1.0 M, pH 8.5±0.1, circa 500 mL/mmol substrate) and allowed to stir for about 12 hours. The resulting solution was washed with ethyl acetate and concentrated in vacuo. The crude product was then collected from reverse phase HPLC (acetonitrile:water, 0.1 TFA or TEAA, 5μ C18). The desired fractions were lyophilized to provide the desired 3'-Coumarinyl carbonate dNTP (CCdNTP) powder. TOF HR-MS m/z $(M-H^+)^-$ Calcd for $[C25H31N3O18P3]^-$=754.0821. Found=754.0807.

Example III

Figure 21:
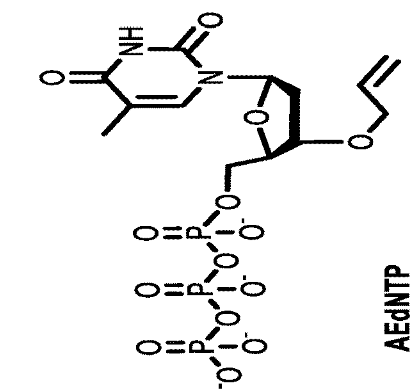
FIG. 21 depicts a synthesis reaction for allyl ether dNTP (AEdNTP).
Figure 21:
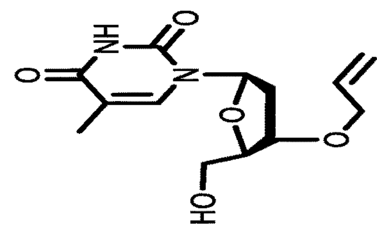
Figure 21:
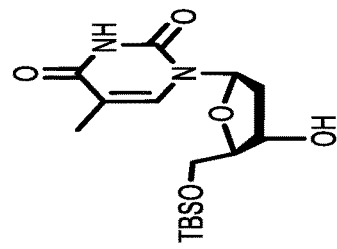

3'-Allyl ether dNTP (AEdNTP) was prepared as follows and as shown in FIG. 21 using the following steps 1-5.

Step 1: 5'-TBS-3'-allyl ether thymidine was prepared using Lebreton's approach as described in Tetrahedron Letters 43 (2002) 8091-8094 hereby incorporated by reference in its entirety.

Step 2: To the 5'-TBS-3'-allyl ether thymidine (1 eq) was added THF (0.1M reaction concentration) and TBAF (1M, 1.2 eq) at room temperature. The reaction was allowed to continue until TLC indicated consumption of starting material. The reaction was stopped with the addition of water. The product was extracted with ethyl acetate. Washing with brine and drying over sodium sulfate provided the crude product, which is the 3'-allyl ether thymidine. Generally, purification by column chromatography (stationary phase of silica gel and mobile phase of ethyl acetate: hexane) is best practice to obtain the pure product.

Step 3: After drying over desiccant, the 3'-allyl ether thymidine (1 eq) was diluted with $POMe_3$ (circa. 0.06 M reaction concentration). The solution was then cooled to 0° C. Fresh $POCl_3$ (2 eq) was added slowly and the reaction was allowed to continue at 0° C. for 1 to 3 hours. See Chem. Rev. 2016, 116, 7854-789; Acta Biochim. Biophys. Acad. Sci. Hung. 1981, 16 (3-4), 131-133; and Yoshikawa, M.; Kato, T.; Takenishi, T. A Novel Method for Phosphorylation of Nucleosides to 5'-Nucleotides. Tetrahedron Lett. 1967, 8 (50), 5065-5068 each of which is hereby incorporated by reference in its entirety.

Step 4: At 0° C., tributylammonium pyrophosphate (0.6 M, 20 eq) was added and the reaction was allowed to stir for about one to five minutes.

Step 5: The solution was then diluted with TEAB (triethylammonium bicarbonate buffer 1.0 M, pH 8.5±0.1, circa 500 mL/mmol substrate) and allowed to stir for about 12 hours. The resulting solution was washed with ethyl acetate and concentrated in vacuo. The crude product was then collected from reverse phase HPLC (acetonitrile:water, 0.1 TFA or TEAA, 5μ C18). The desired fractions were lyophilized to provide the desired 3'-allyl ether dNTP (AEdNTP) powder. TOF HR-MS m/z $(M-H^+)^-$ Calcd for $[C13H20N2O14P3]^-$=521.0133. Found=521.008.

The invention claimed is:

1. A method of making a polynucleotide comprising combining (1) a selected nucleotide analog represented by formula I:

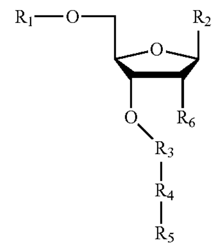

wherein:

R1 is H, a monophosphate, a diphosphate, a triphosphate or a nucleic acid,

R2 is a nucleobase or a modified nucleobase,

R3 is a cleavable moiety,

R4 is absent or a linker moiety,

R5 is absent or a detectable moiety, and

R6 is H or OH, (2) one or more cations, and (3) a template-independent polymerase in an aqueous reaction medium including a target substrate comprising an initiator sequence having a 3' terminal nucleotide, such that the template-independent polymerase interacts with the target substrate under conditions which covalently adds one of the selected nucleotide analog to the 3' terminal nucleotide.

2. The method of claim 1 further including removing the cleavable moiety from the 3' terminal nucleotide analog of the extended target substrate and restoring a free 3'-OH group of the 3' terminal nucleotide.

3. The method of claim 2 further including repeatedly introducing a subsequent selected nucleotide analog to the aqueous reaction medium under conditions which enzymatically add one of the subsequent selected nucleotide analog to the target substrate and removing the cleavable moiety from the 3' terminal nucleotide analog of the extended target substrate and restoring a free 3'-OH group of the 3' terminal nucleotide until the polynucleotide is formed.

4. The method of claim 1 wherein the template-independent polymerase is a template-independent DNA or RNA polymerase.

5. The method of claim 1 wherein the template-independent polymerase is a template-independent DNA polymerase.

6. The method of claim 1 wherein the template-independent polymerase is a terminal deoxynucleotidyl transferase (TdT).

7. The method of claim 1 wherein the cleavable moiety comprises a protective group.

8. The method of claim 1 wherein the cleavable moiety is photo cleavable, thermo-cleavable, electrochemical cleavable, transition metal cleavable or cleavable by a change in pH.

9. The method of claim 1 wherein formula I comprises the linker moiety, wherein the linker moiety comprises a removable group selected from the group consisting of ortho-nitrobenzyl, quinone, coumarin, an aminophenol derivative, an azidomethylene derivative, and a ketal group.

10. The method of claim 1 wherein formula I comprises the linker moiety, wherein the linker moiety is produced from di NHS ester, di isocyanate, di isothiocyanate, di acid halide, di anhydride, bis[2-(N-succinimidyl-oxycarbonyloxy)ethyl] sulfone, Di(N-succinimidyl) glutarate, Sebacic acid bis(N-succinimidyl) ester, p-Phenylene diisothiocyanate, 4,7,10,13,16,19,22,25,32,35,38,41,44,47,50,53-Hexadecaoxa-28,29dithiahexapentacontanedioic acid di-N-succinimidyl ester, DTSSP (3,3'-dithiobis(sulfosuccinimidyl propionate)), Sulfo-EGS (ethylene glycol bis(sulfosuccinimidyl succinate)), DST (disuccinimidyl tartrate), BS(PEG)9 (PEGylated bis(sulfosuccinimidyl)suberate), BS(PEG)5 (PEGylated bis(sulfosuccinimidyl)suberate), Dimethyl 3,3'-dithiopropionimidate, 4,4'-Diisothiocyanatostilbene-2,2'-disulfonic acid, 3,3'-Dithiodipropionic acid di(N-hydroxysuccinimide ester), Dimethyl pimelimidate dihydrochloride, Ethylene glycol-bis(succinic acid N-hydroxysuccinimide ester), Suberic acid bis(N-hydroxysuccinimide ester), Suberic acid bis(3-sulfo-N-hydroxysuccinimide ester); di Maleimide, di haloacetyl, di pyridyldithiol, di vinylsulfone, di alkene with radical, 1,4-Bis[3-(2-pyridyldithio)propionamido]butane, BMOE (bis-maleimidoethane), BM(PEG)2 (1,8-bismaleimido-diethyleneglycol), BM(PEG)3 (1,11-bismaleimido-triethyleneglycol), DTME (dithio-bis-maleimidoethane); NHS ester, isocynanate, isothiocyanate, acid halide, or anhydride and maleimide, haloacetyl, pyridyldithiol, vinylsulfone, or alkene with radical, Sulfo-SMPB (sulfosuccinimidyl 4-(N-maleimidophenyl)butyrate), Sulfo-SIAB (sulfosuccinimidyl (4-iodoacetyl)aminobenzoate), Sulfo-N-succinimidyl 4-maleimidobutyrate, Sulfo-MBS (m-maleimidobenzoyl-N-hydroxysulfosuccinimide ester), Sulfo-LC-SPDP (sulfosuccinimidyl 6-[3'-(2-pyridyldithio)propionamido]hexanoate), Sulfo-KMUS (N-(κ-maleimidoundecanoyloxy) sulfosuccinimide ester), Sulfo-EMCS (N-(ε-maleimidocaproyloxy) sulfosuccinimide ester), SMPT (4-succinimidyloxycarbonyl-alpha-methyl-alpha(2-pyridyldithio)toluene), SMPH (succinimidyl-6-((b-maleimidopropionamido)hexanoate), SM(PEG) 24 (PEGylated, long-chain SMCC crosslinker), SIAB (N-succinimidyl (4-iodoacetyl)aminobenzoate), SBAP (succinimidyl 3-(bromoacetamido)propionate), PEG4-SPDP (PEGylated, long-chain SPDP crosslinker), PEG12-SPDP (PEGylated, long-chain SPDP crosslinker), O—[N-(3-Maleimidopropionyl)aminoethyl]-O'-[3-(N-succinimidyloxy)-3-oxopropyl]triethylene glycol, O—[N-(3-Maleimidopropionyl)aminoethyl]-O'-[3-(N-succinimidyloxy)-3-oxopropyl]heptacosaethylene glycol, Maleimidoacetic acid N-hydroxysuccinimide ester, Maleimide-PEG8-succinimidyl ester, Maleimide-PEG6-succinimidyl ester, Maleimide-PEG2-succinimidyl ester, Maleimide-PEG12-succinimidyl ester, LC-SPDP (succinimidyl 6-[3(2-pyridyldithio)propionamido]hexanoate), LC-SMCC (succinimidyl-4-(N-maleimidomethyl)cyclohexane-1-carboxy-(6-amidocaproate)), Iodoacetic acid N-hydroxysuccinimide ester, Bromoacetic acid N-hydroxysuccinimide ester, 6-Maleimidohexanoic acid N-hydroxysuccinimide ester, 4-Maleimidobutyric acid N-hydroxysuccinimide ester, 4-(4-Maleimidophenyl)butyric acid N-hydroxysuccinimide ester, 3-Maleimidopropionic acid N-hydroxysuccinimide ester, 3-(2-Pyridyldithio)propionic acid N-hydroxysuccinimide ester; carbodiimide; isocyanate and maleimide, haloacetyl, pyridyldithiol, vinylsulfone, or alkene with radical.

11. The method of claim 1 wherein formula I comprises the detectable moiety.

12. The method of claim 11 wherein the detectable moiety comprises a fluorophore comprising Methoxycoumarin, Dansyl, Pyrene, Alexa Fluor 350, AMCA, Marina Blue dye, Dapoxyl dye, Dialkylaminocoumarin, Bimane, Hydroxycoumarin, Cascade Blue dye, Pacific Orange dye, Alexa Fluor 405, Cascade Yellow dye, Pacific Blue dye, PyMPO, Alexa Fluor 430, NBD, QSY 35, Fluorescein, Alexa Fluor 488, Oregon Green 488, BODIPY 493/503, Rhodamine Green dye, BODIPY FL, 2',7'-Dichloro-, fluorescein, Oregon Green 514, Alexa Fluor 514, 4',5'-Dichloro-, 2',7'-dimethoxy-, fluorescein (JOE), Eosin, Rhodamine 6G, BODIPY R6G, Alexa Fluor 532, BODIPY 530/550, BODIPY TMR, Alexa Fluor 555, Tetramethyl-, rhodamine (TMR), Alexa Fluor 546, BODIPY 558/568, QSY 7, QSY 9, BODIPY 564/570, Lissamine rhodamine B, Rhodamine Red dye, BODIPY 576/589, Alexa Fluor 568, X-rhodamine, BODIPY 581/591, BODIPY TR, Alexa Fluor 594, Texas Red dye, Naphthofluorescein, Alexa Fluor 610, BODIPY 630/650, Malachite green, Alexa Fluor 633, Alexa Fluor 635, BODIPY 650/665, Alexa Fluor 647, QSY 21, Alexa Fluor 660, Alexa Fluor 680, Alexa Fluor 700, Alexa Fluor 750, Alexa Fluor 790 or a derivative thereof.

13. The method of claim 7 wherein the protective group comprises an ether, ester, carbonate, carbamate or silyl ether or a derivative thereof.

14. The method of claim 11 wherein the detectable moiety is a fluorescent moiety.

* * * * *